(12) United States Patent
Steinbach

(10) Patent No.: US 8,568,360 B2
(45) Date of Patent: Oct. 29, 2013

(54) PROGRAMMABLE IMPLANTABLE PUMP DESIGN

(75) Inventor: Bernd Steinbach, Friedberg (DE)

(73) Assignee: Palyon Medical (BVI) Limited (VG)

( * ) Notice: Subject to any disclaimer, the term of this patent is extended or adjusted under 35 U.S.C. 154(b) by 0 days.

(21) Appl. No.: 13/338,673

(22) Filed: Dec. 28, 2011

(65) Prior Publication Data

US 2013/0172810 A1    Jul. 4, 2013

(51) Int. Cl.
*A61M 1/00* (2006.01)

(52) U.S. Cl.
USPC ........................................................ 604/151

(58) Field of Classification Search
USPC ........................................................ 604/67
See application file for complete search history.

(56) References Cited

U.S. PATENT DOCUMENTS

| | | | |
|---|---|---|---|
| 3,951,147 A | 4/1976 | Tucker et al. | |
| 4,077,405 A | 3/1978 | Haerten et al. | |
| 4,187,870 A | 2/1980 | Akkerman | |
| 4,193,397 A | 3/1980 | Tucker et al. | |
| 4,270,532 A | 6/1981 | Franetzki et al. | |
| 4,299,220 A | 11/1981 | Dorman | |
| 4,373,527 A | 2/1983 | Fischell | |
| 4,411,651 A | 10/1983 | Schulman | |
| 4,443,218 A | 4/1984 | DeCant, Jr. et al. | |
| 4,447,224 A | 5/1984 | DeCant, Jr. et al. | |
| 4,486,190 A | 12/1984 | Reinicke | |
| 4,496,343 A | 1/1985 | Prosl et al. | |
| 4,511,163 A | 4/1985 | Harris et al. | |
| 4,557,726 A | 12/1985 | Reinicke | |
| 4,573,994 A | 3/1986 | Fischell et al. | |
| 4,626,244 A | 12/1986 | Reinicke | |
| 4,627,840 A | 12/1986 | Cuadra et al. | |
| 4,639,244 A | 1/1987 | Rizk et al. | |
| 4,661,097 A | 4/1987 | Fischell et al. | |
| 4,671,320 A | 6/1987 | Grifols Lucas | |
| 4,685,902 A | 8/1987 | Edwards et al. | |
| 4,714,462 A | 12/1987 | DiDomenico | |
| 4,718,893 A | 1/1988 | Dorman et al. | |

(Continued)

FOREIGN PATENT DOCUMENTS

| | | |
|---|---|---|
| DE | 9107030 | 6/1991 |
| EP | 0045668 | 2/1982 |

(Continued)

OTHER PUBLICATIONS

International Search Report and Written Opinion for Application No. PCT/EP2012/068105 dated Dec. 19, 2012.

(Continued)

*Primary Examiner* — Jason Flick
(74) *Attorney, Agent, or Firm* — Lerner, David, Littenberg, Krumholz & Mentlik, LLP

(57) ABSTRACT

A programmable implantable pump is disclosed. The pump includes an implantable pump and a hermetically sealed module. The module provides for varying flow rates of fluid being dispensed from the pump or may provide for a constant flow rate of such fluid. In the case of varying flow rate capabilities, the module preferably includes one or more sensors to determine information relating to the pressure of the fluid, electronics for analyzing the pressure information and determining the flow rate of the fluid, and a mechanism for physically altering the flow rate. Methods of dispensing a medicament to a patient utilizing such a system are also disclosed, as are variations of the pump system.

20 Claims, 37 Drawing Sheets

(56) References Cited

U.S. PATENT DOCUMENTS

| | | |
|---|---|---|
| 4,738,665 A | 4/1988 | Shepard |
| 4,772,263 A | 9/1988 | Dorman et al. |
| 4,772,270 A | 9/1988 | Wiita et al. |
| 4,838,887 A | 6/1989 | Idriss |
| 4,915,690 A | 4/1990 | Cone et al. |
| 4,931,050 A | 6/1990 | Idriss |
| 4,955,861 A | 9/1990 | Enegren et al. |
| 4,969,873 A | 11/1990 | Steinbach et al. |
| 4,978,338 A | 12/1990 | Melsky et al. |
| 5,015,374 A | 5/1991 | Mathieu et al. |
| 5,045,060 A | 9/1991 | Melsky et al. |
| 5,061,242 A | 10/1991 | Sampson |
| 5,067,943 A | 11/1991 | Burke |
| 5,085,656 A | 2/1992 | Polaschegg |
| 5,088,983 A | 2/1992 | Burke |
| 5,135,498 A | 8/1992 | Kam et al. |
| 5,146,933 A | 9/1992 | Boyd |
| 5,147,483 A | 9/1992 | Melsky et al. |
| 5,163,920 A | 11/1992 | Olive |
| 5,205,819 A | 4/1993 | Ross et al. |
| 5,207,666 A | 5/1993 | Idriss et al. |
| 5,217,442 A | 6/1993 | Davis |
| 5,242,406 A | 9/1993 | Gross et al. |
| 5,336,194 A | 8/1994 | Polaschegg et al. |
| 5,395,324 A | 3/1995 | Hinrichs et al. |
| 5,405,339 A | 4/1995 | Kohnen et al. |
| 5,445,616 A | 8/1995 | Kratoska et al. |
| 5,462,525 A | 10/1995 | Srisathapat et al. |
| 5,474,552 A | 12/1995 | Palti |
| 5,549,866 A | 8/1996 | Grifols Lucas |
| 5,569,186 A | 10/1996 | Lord et al. |
| 5,575,770 A | 11/1996 | Melsky et al. |
| 5,637,102 A | 6/1997 | Tolkoff et al. |
| 5,665,070 A | 9/1997 | McPhee |
| 5,667,504 A | 9/1997 | Baumann et al. |
| 5,704,915 A | 1/1998 | Melsky et al. |
| 5,722,957 A | 3/1998 | Steinbach |
| 5,766,150 A | 6/1998 | Langkau |
| 5,769,823 A | 6/1998 | Otto et al. |
| 5,785,681 A | 7/1998 | Indravudh |
| 5,785,688 A | 7/1998 | Joshi et al. |
| 5,792,104 A | 8/1998 | Speckman et al. |
| 5,814,019 A | 9/1998 | Steinbach et al. |
| 5,836,915 A | 11/1998 | Steinbach et al. |
| 5,840,063 A | 11/1998 | Flaherty |
| 5,904,666 A | 5/1999 | DeDecker et al. |
| 5,931,829 A | 8/1999 | Burbank et al. |
| 5,949,632 A | 9/1999 | Barreras, Sr. et al. |
| 5,957,891 A | 9/1999 | Kriesel et al. |
| 5,980,508 A | 11/1999 | Cardamone et al. |
| 6,048,328 A | 4/2000 | Haller et al. |
| 6,166,518 A | 12/2000 | Echarri et al. |
| 6,181,105 B1 | 1/2001 | Cutolo et al. |
| 6,203,523 B1 | 3/2001 | Haller et al. |
| 6,213,972 B1 | 4/2001 | Butterfield et al. |
| 6,238,369 B1 | 5/2001 | Burbank et al. |
| 6,278,258 B1 | 8/2001 | Echarri et al. |
| 6,280,416 B1 | 8/2001 | Van Antwerp et al. |
| 6,283,944 B1 | 9/2001 | McMullen et al. |
| 6,349,740 B1 | 2/2002 | Cho et al. |
| 6,416,291 B1 | 7/2002 | Butterfield et al. |
| 6,416,495 B1 | 7/2002 | Kriesel et al. |
| 6,423,029 B1 | 7/2002 | Elsberry |
| 6,464,671 B1 | 10/2002 | Elver et al. |
| 6,471,645 B1 | 10/2002 | Warkentin et al. |
| 6,471,675 B1 | 10/2002 | Rogers et al. |
| 6,488,652 B1 | 12/2002 | Weijand et al. |
| 6,558,320 B1 | 5/2003 | Causey, III et al. |
| 6,562,001 B2 | 5/2003 | Lebel et al. |
| 6,572,583 B1 | 6/2003 | Olsen et al. |
| 6,577,899 B2 | 6/2003 | Lebel et al. |
| 6,589,205 B1 | 7/2003 | Meadows |
| 6,620,151 B2 | 9/2003 | Blischak et al. |
| 6,638,263 B1 | 10/2003 | Theeuwes et al. |
| 6,641,533 B2 | 11/2003 | Causey, III et al. |
| 6,648,821 B2 | 11/2003 | Lebel et al. |
| 6,652,510 B2 | 11/2003 | Lord et al. |
| 6,664,763 B2 | 12/2003 | Echarri et al. |
| 6,673,091 B1 | 1/2004 | Shaffer et al. |
| 6,676,104 B2 | 1/2004 | Tillander |
| 6,687,546 B2 | 2/2004 | Lebel et al. |
| 6,702,779 B2 | 3/2004 | Connelly et al. |
| 6,719,739 B2 | 4/2004 | Verbeek et al. |
| 6,749,587 B2 | 6/2004 | Flaherty |
| 6,764,472 B1 | 7/2004 | Burke et al. |
| 6,805,687 B2 | 10/2004 | Dextradeur et al. |
| 6,814,547 B2 | 11/2004 | Childers et al. |
| 6,869,275 B2 | 3/2005 | Dante et al. |
| 6,878,135 B1 | 4/2005 | Haller et al. |
| 6,895,419 B1 | 5/2005 | Cargin, Jr. et al. |
| 6,902,544 B2 | 6/2005 | Ludin et al. |
| 6,932,114 B2 | 8/2005 | Sparks |
| 6,997,919 B2 | 2/2006 | Olsen et al. |
| 7,004,924 B1 | 2/2006 | Brugger et al. |
| 7,018,384 B2 | 3/2006 | Skakoon |
| 7,083,593 B2 | 8/2006 | Stultz |
| 7,108,686 B2 | 9/2006 | Burke et al. |
| 7,150,741 B2 | 12/2006 | Erickson et al. |
| 7,214,221 B2 | 5/2007 | Fentress et al. |
| 7,367,968 B2 | 5/2008 | Rosenberg et al. |
| 7,637,892 B2 | 12/2009 | Steinbach et al. |
| 2002/0022759 A1 | 2/2002 | Forsell |
| 2002/0072721 A1 | 6/2002 | Verbeek et al. |
| 2002/0087113 A1 | 7/2002 | Hartlaub |
| 2002/0120186 A1 | 8/2002 | Keimel |
| 2002/0156463 A1 | 10/2002 | Berrigan |
| 2002/0193751 A1 | 12/2002 | Theeuwes et al. |
| 2003/0171711 A1 | 9/2003 | Rohr et al. |
| 2003/0208184 A1 | 11/2003 | Burke et al. |
| 2003/0214199 A1 | 11/2003 | Heim et al. |
| 2003/0216683 A1 | 11/2003 | Shekalim |
| 2004/0005433 A1 | 1/2004 | Iguchi et al. |
| 2004/0005931 A1 | 1/2004 | Wang et al. |
| 2004/0054333 A1 | 3/2004 | Theeuwes |
| 2004/0055648 A1 | 3/2004 | Erickson |
| 2004/0059315 A1 | 3/2004 | Erickson et al. |
| 2004/0068224 A1 | 4/2004 | Couvillon et al. |
| 2004/0143242 A1 | 7/2004 | Ludin et al. |
| 2004/0153029 A1 | 8/2004 | Blischak et al. |
| 2004/0202691 A1 | 10/2004 | Richard |
| 2004/0204673 A1 | 10/2004 | Flaherty |
| 2004/0242956 A1 | 12/2004 | Scorvo |
| 2004/0254565 A1 | 12/2004 | Russell |
| 2005/0011374 A1 | 1/2005 | Dejakum et al. |
| 2005/0024175 A1 | 2/2005 | Gray et al. |
| 2005/0037078 A1 | 2/2005 | Kuo et al. |
| 2005/0038396 A1 | 2/2005 | Claude et al. |
| 2005/0054988 A1 | 3/2005 | Rosenberg et al. |
| 2005/0065500 A1 | 3/2005 | Couvillon et al. |
| 2005/0070883 A1 | 3/2005 | Brown et al. |
| 2005/0075624 A1 | 4/2005 | Miesel |
| 2005/0101942 A1 | 5/2005 | Gillis et al. |
| 2005/0113745 A1 | 5/2005 | Stultz |
| 2005/0113892 A1 | 5/2005 | Sproul |
| 2005/0187515 A1 | 8/2005 | Varrichio et al. |
| 2005/0197652 A1 | 9/2005 | Nat |
| 2005/0273081 A1 | 12/2005 | Olsen |
| 2005/0273082 A1 | 12/2005 | Olsen |
| 2005/0273083 A1* | 12/2005 | Lebel et al. ............... 604/891.1 |
| 2006/0089619 A1 | 4/2006 | Ginggen |
| 2006/0253135 A1 | 11/2006 | Ortiz |
| 2006/0259015 A1 | 11/2006 | Steinbach |
| 2006/0259016 A1 | 11/2006 | Steinbach |
| 2006/0271021 A1 | 11/2006 | Steinbach |
| 2006/0271022 A1 | 11/2006 | Steinbach et al. |
| 2007/0005044 A1 | 1/2007 | Steinbach et al. |
| 2007/0112328 A1 | 5/2007 | Steinbach et al. |
| 2009/0113996 A1 | 5/2009 | Wang et al. |
| 2010/0069892 A1* | 3/2010 | Steinbach et al. ......... 604/891.1 |
| 2010/0185175 A1* | 7/2010 | Kamen et al. ................ 604/504 |
| 2010/0280501 A1 | 11/2010 | Young et al. |

(56) References Cited

U.S. PATENT DOCUMENTS

FOREIGN PATENT DOCUMENTS

| | | | |
|---|---|---|---|
| EP | 0344895 | A2 | 12/1989 |
| FR | 2628639 | | 9/1989 |
| FR | 2860438 | A1 | 4/2005 |
| JP | 10299660 | A | 11/1998 |
| JP | 2002-292683 | | 10/2002 |
| JP | 2002541573 | A | 12/2002 |
| WO | 0066204 | A1 | 11/2000 |
| WO | 03/068049 | | 8/2003 |
| WO | 03081762 | A1 | 10/2003 |
| WO | 2005007223 | | 1/2005 |
| WO | 2005044343 | | 5/2005 |
| WO | 2005079885 | | 9/2005 |
| WO | 2006/122330 | | 11/2006 |

OTHER PUBLICATIONS

International Search Report and Written Opinion for Application No. PCT/EP2012/068109 dated Dec. 19, 2012.
Elliptec Resonant Actuator, X15G Preliminary Datasheet, Oct. 2004.
Website printout: www.medtronic.com/neuro/paintherapies/pain <http://www.medtronic.com/neuro/paintherapies/pain>; N'Vision Programmer Discussion, (Jun. 15, 2005).
International Search Report, PCT/US2007/024026 dated Jul. 21, 2008.
International Search Report, PCT/US06/18981 dated Jan. 16, 2007.
Extended European Search Report for Application No. 06770454.4 dated Nov. 7, 2012.
Supplementary Partial European Search Report for Application No. 06770454 dated Oct. 29, 2012.
Extended European Search Report for Application No. EP07862066 dated May 23, 2013.

* cited by examiner

PROGRAMMABLE IMPLANTABLE PUMP DESIGN

BACKGROUND OF THE INVENTION

The present invention relates to implantable devices, more particularly, programmable implantable pumps allowing for variable flow rates in delivering medication or other fluid to a selected site in the body of a patient.

Implantable pumps have been well known and widely utilized for many years. Typically, pumps of this type are implanted into patients who require the delivery of active substances or medication fluids to specific areas of their body. For example, patients that are experiencing severe pain may require pain killers daily or multiple times per day. Absent the use of an implantable pump or the like, a patient of this type would be subject to one or more painful injections of such medication fluids. In the case of pain associated with more remote areas of the body, such as the spine, these injections may be extremely difficult to administer and particularly painful for the patient. In certain instances, proper application of such medication may be impossible. Furthermore, attempting to treat conditions such as this through oral or intravascular administration of medication often requires higher doses of medication and may cause severe side effects. Therefore, it is widely recognized that utilizing an implantable pump may be beneficial to both a patient and a treating physician.

Many implantable pump designs have been proposed. For example, commonly invented U.S. Pat. No. 4,969,873 ("the '873 Patent"), the disclosure of which is hereby incorporated by reference herein, teaches one such design. The '873 Patent is an example of a constant flow pump, which typically includes a housing having two chambers, a first chamber for holding a specific medication fluid to be administered and a second chamber for holding a propellant. A flexible membrane preferably separates the two chambers such that expansion of the propellant in the second chamber pushes the medication fluid out of the first chamber. It is to be understood that the propellant typically expands under normal body temperature. This type of pump also typically includes an outlet opening connected to a catheter for directing the medication fluid to the desired area of the body, a replenishment opening for allowing for refill of the medication fluid into the first chamber and a bolus opening for allowing the direct introduction of a substance through the catheter without introduction into the first chamber. Both the replenishment opening and the bolus opening are typically covered by a septum that allows a needle or similar device to be passed through it, but which properly seals the opening upon removal of the device. As pumps of this type provide a constant flow of medication fluid to the specific area of the body, they must be refilled periodically with the proper concentration of medication fluids suited for extended release.

Although clearly beneficial to patients and doctors that utilize them, constant flow pumps generally have one major problem, i.e., that only a single flow rate can be achieved from the pump. Thus, implantable pumps have also been developed, which allow for variable flow rates of medication therefrom. These pumps are typically referred to as programmable pumps, and have exhibited many different types of designs. For instance, in a solenoid pump, the flow rate of medication fluid can be controlled by changing the stroke rate of the pump. In a peristaltic pump, the flow rate can be controlled by changing the roller velocity of the pump. Likewise, pumps of the constant flow type have been modified to allow for a variable and programmable flow rate. For instance, commonly owned U.S. Pat. No. 7,637,892 ("the '892 Patent") teaches such a design. The '892 Patent, as well as related U.S. patent application Ser. Nos. 11/125,586; 11/126,101; and 11/157,437 are each incorporated herein by reference. In each case, the benefit of providing variable flow is at the forefront, so that differing levels of medication can be delivered to the patient at different times.

In the '892 Patent, a constant flow-type pump assembly is modified to include a module that converts the constant flow pump into a programmable pump. That control module includes, inter alia, two pressure sensors, a constant flow capillary, and a valve assembly. The pressure centers are utilized to measure pressure directly from a medication chamber, and pressure just prior to entering the valve assembly. These pressure readings are utilized by a computing unit, which in turn causes a motor to operate the valve assembly to allow lesser or greater flow from the pump. The capillary preferably ensures that a maximum flow rate can only be achieved from the pump. The pump taught in the '892 Patent is indeed a useful programmable pump, but one which may be improved.

One area in which the pump taught in the '892 Patent, as well as pumps taught in other prior art references, can be improved is in allowing for finer adjustment of flow rate from the pump, which is often difficult or impossible. For instance, a pump of the type taught in the '892 Patent may exhibit a nonlinear relationship between movement of the valve and actual flow rate from the pump, which can lead to small changes in valve position resulting in major changes in flow. Of course, a more preferable valve distance and flow relationship would be of the linear type, where the distance is gradually related to the flow rate. Another area in which prior art programmable pumps can be improved is in the sealing of certain components from the body environment in which the pump is implanted. This may be particularly important in ensuring constant operation of the pump, as well as in ensuring the safety of the patient.

Therefore, there exists a need for an improved programmable implantable pump design.

BRIEF SUMMARY OF THE INVENTION

A first aspect of the present invention is a programmable pump for dispensing a fluid at varying flow rates to a patient including a constant flow module including a first chamber housing the fluid, a first opening in fluid communication with the first chamber and a second opening in fluid communication with a catheter and a hermetically sealed control module attached to the constant flow module and including a motor assembly and valve block, the valve block being in fluid communication with the first and second openings, the motor assembly having a stepper motor, a valve connected with the stepper motor, and a bellows surrounding a portion of the valve. The flow rate of the fluid dispelled from the active substance chamber is preferably affected by varying positioning of the valve.

In other embodiments of the first aspect the bellows may surround the portion of the valve in all positions of the valve. The bellows may be tubular and of varying length. The valve may include a valve bushing and a valve stem extending through the valve bushing and having a tapered end. The motor assembly may further include an o-ring surrounding the valve bushing. The constant flow module may further includes a second chamber separated from the active substance chamber by a first flexible membrane. The second chamber may be filled with a propellant that acts upon the flexible membrane to push the fluid from the first chamber through first opening. During operation of the pump, fluid dispelled from the first chamber passes through the first opening, through into the valve block, into contact with the valve, out of the valve block, into the second opening and through the catheter. The control module may further include a first pressure sensor for monitoring the pressure of the fluid in the first chamber and a second pressure sensor for monitoring the pressure of the fluid in the valve block. The constant flow module may further include a fixed flow resistor. The fixed flow resistor includes a filter and a capillary, and fluid dispelled from the first chamber passes through the fixed flow resistor prior to passing through the first opening. An enclosure top may be attached to the constant flow module and covering the control module. The control module may further include a processor for determining operation of the motor. The pump may further include a circumferentially wrapped antenna extending around a perimeter of the constant flow module that is in communication with the processor. The control module may further include a positioning sensor capable of determining the positioning of the valve. The catheter may include a portion fixed to the constant flow module. A union nut may be screwed to the constant flow module and holding the control module to the constant flow module. A gasket may be held between the constant flow module and control module. The control module may further include first and second pressure sensors, first and second batteries, a circuit board, and a buzzer. The first and second pressure sensors, first and second batteries, circuit board, buzzer and stepper motor may be electrically connected to each other via a flexible conductive element.

BRIEF DESCRIPTION OF THE DRAWINGS

For more complete appreciation of the subject matter of the present invention and the various advantages thereof can be realized by reference to the following detailed description in which reference is made to the accompanying drawings in which.

DETAILED DESCRIPTION

In describing the preferred embodiments of the subject matter illustrated and to be described with respect to the drawings, specific terminology will be used for the sake of clarity. However, the invention is not intended to be limited to any specific terms used herein, and it is to be understood that each specific term includes all technical equivalents which operate in a similar matter to accomplish a similar purpose.

Figure 1:
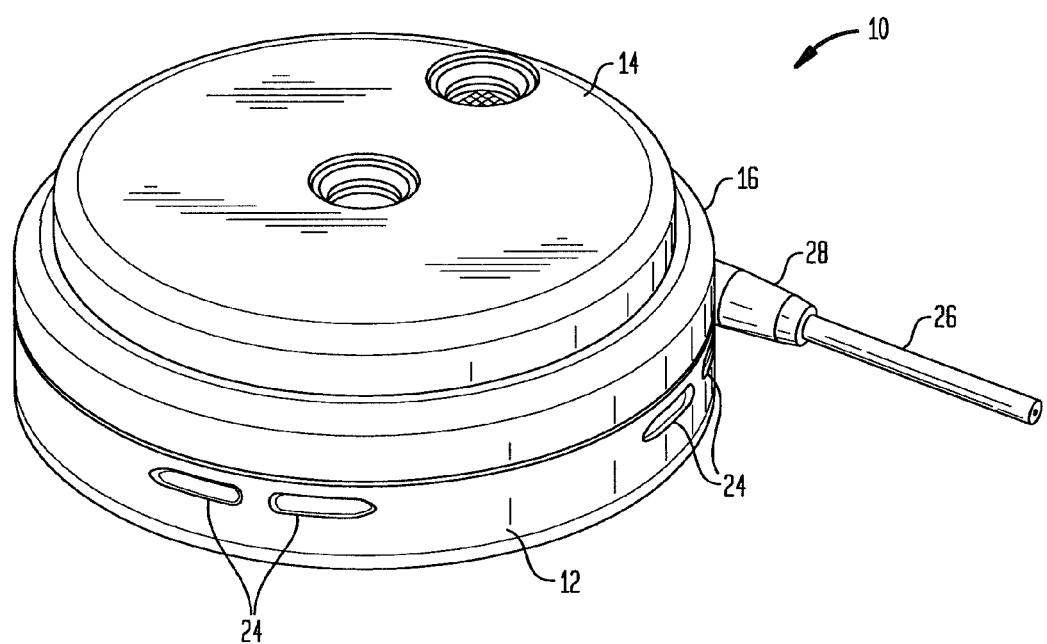
FIG. 1 is a perspective view of a programmable implantable pump in accordance with one embodiment of the present invention.
Figure 2:
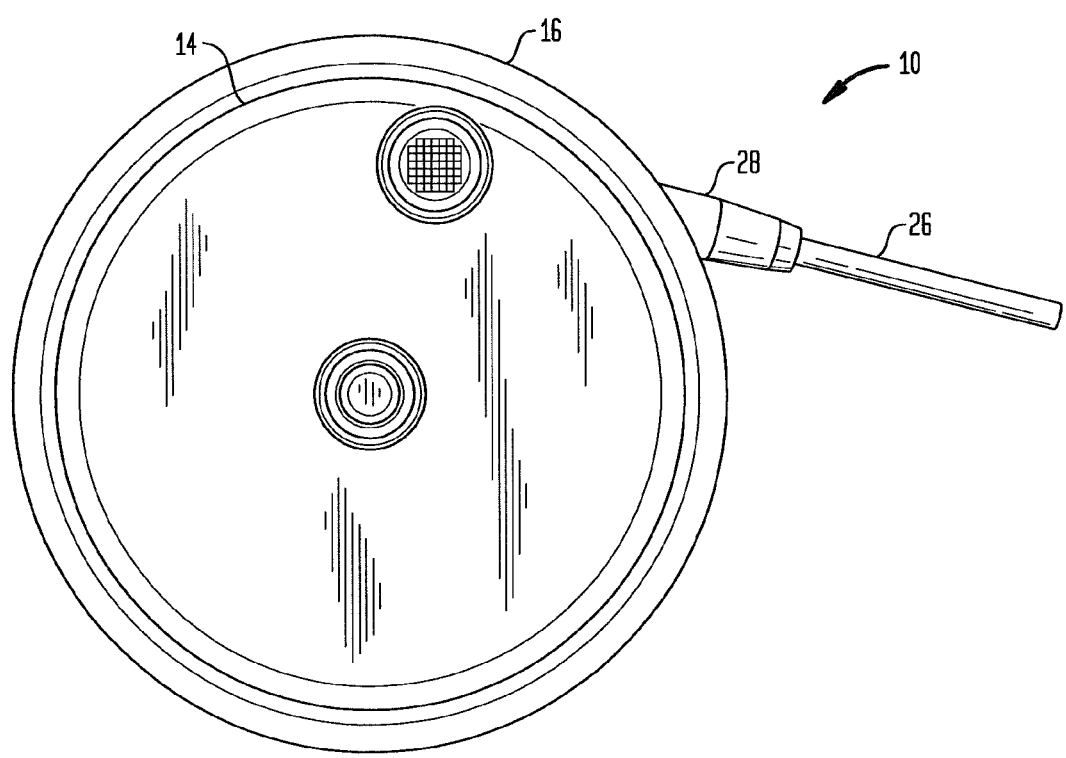
FIG. 2 is a top view of the programmable implantable pump shown in FIG. 1.
Figure 3:
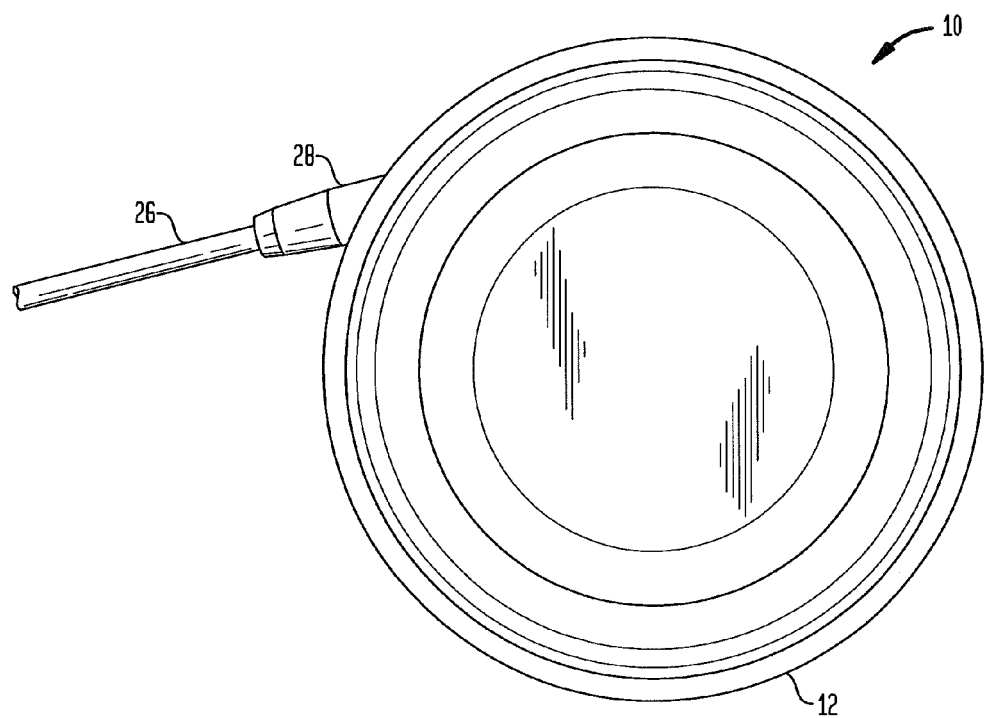
FIG. 3 is a bottom view of the implantable programmable pump shown in FIG. 1.
Figure 4:
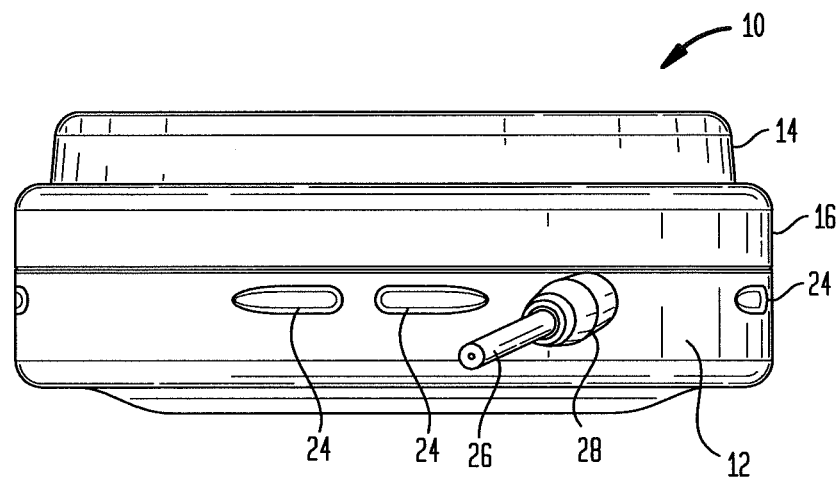
FIG. 4 is a right side view of the programmable implantable pump shown in FIG. 1.
Figure 5:
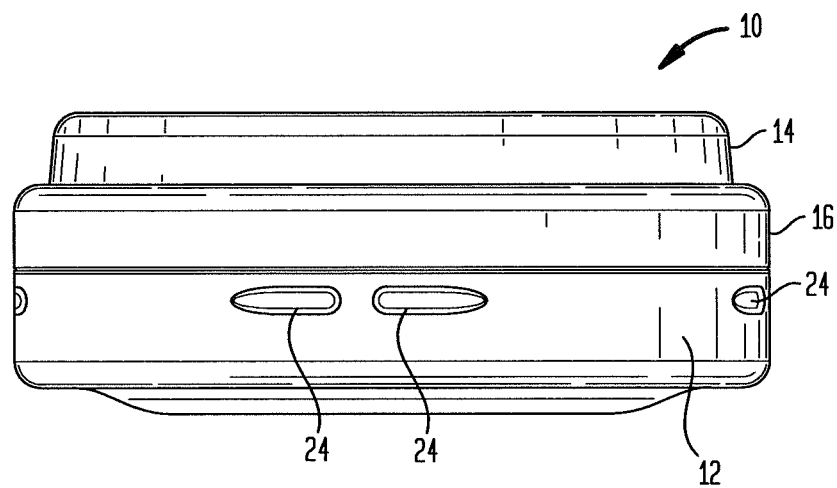
FIG. 5 is a left side view of the programmable implantable pump shown in FIG. 1.
Figure 6:
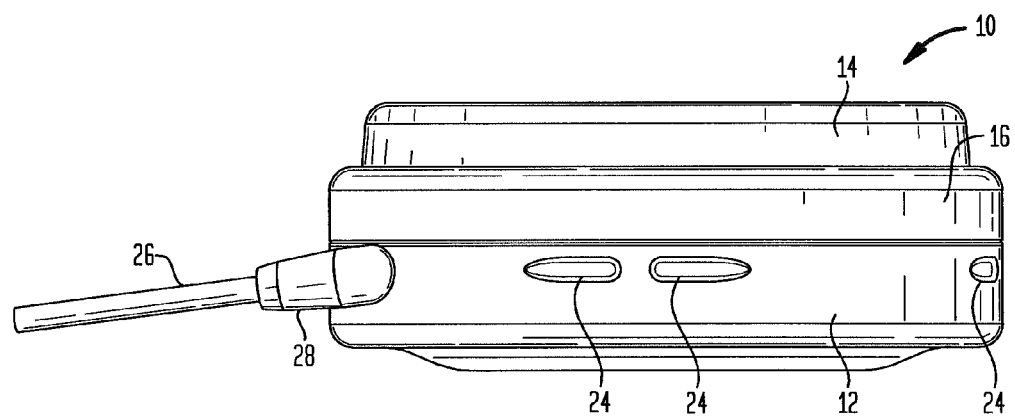
FIG. 6 is a rear view of the programmable implantable pump shown in FIG. 1.
Figure 7:
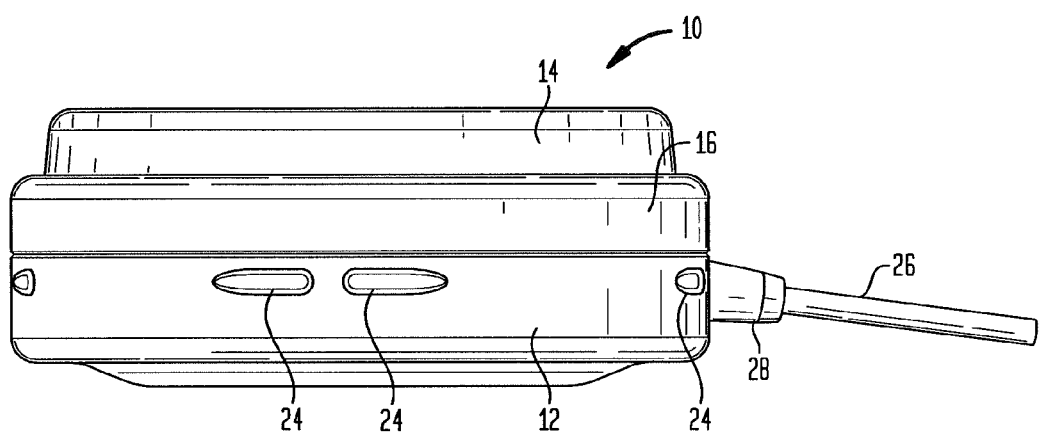
FIG. 7 is a front view of the programmable implantable pump shown in FIG. 1.
Figure 8:
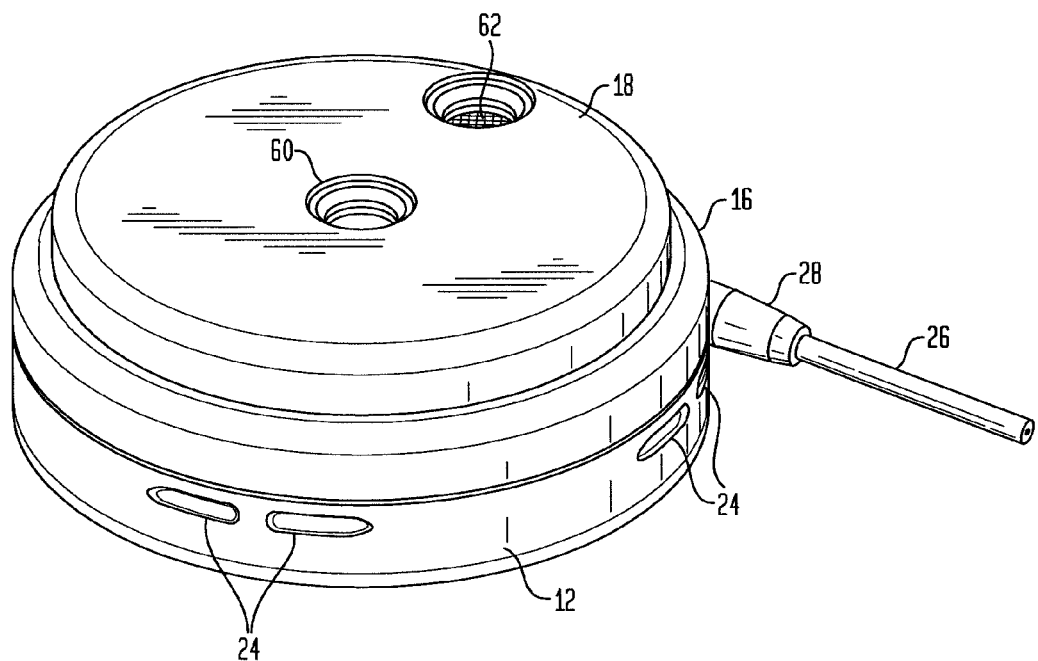
FIG. 8 is a perspective view of the implantable programmable pump shown in FIG. 1 with an enclosure top removed therefrom.
Figure 30:
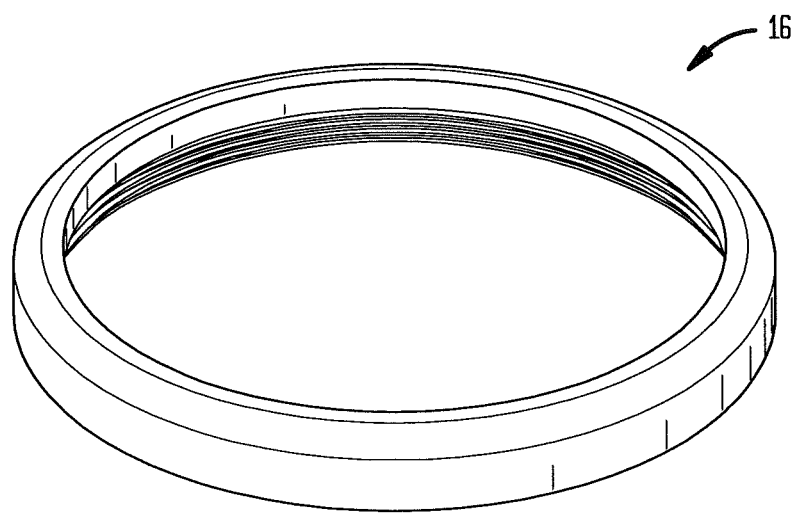
FIG. 30 is a perspective view of union nut included in the pump shown in FIG. 1.

Referring to the drawings, wherein like reference numerals refer to like elements, there is shown in FIGS. 1-7 a programmable implantable pump designated generally by reference numeral 10. As shown in those figures, pump 10 includes a constant flow module assembly 12 (shown alone in FIGS. 9-11), an enclosure top 14, and a union nut 16 (shown alone in FIG. 30). Moreover, as best shown in FIG. 8, where enclosure top 14 has been removed, pump 10 includes a control module assembly 18 engaged with the top portion of constant flow module 12.

Figure 9:
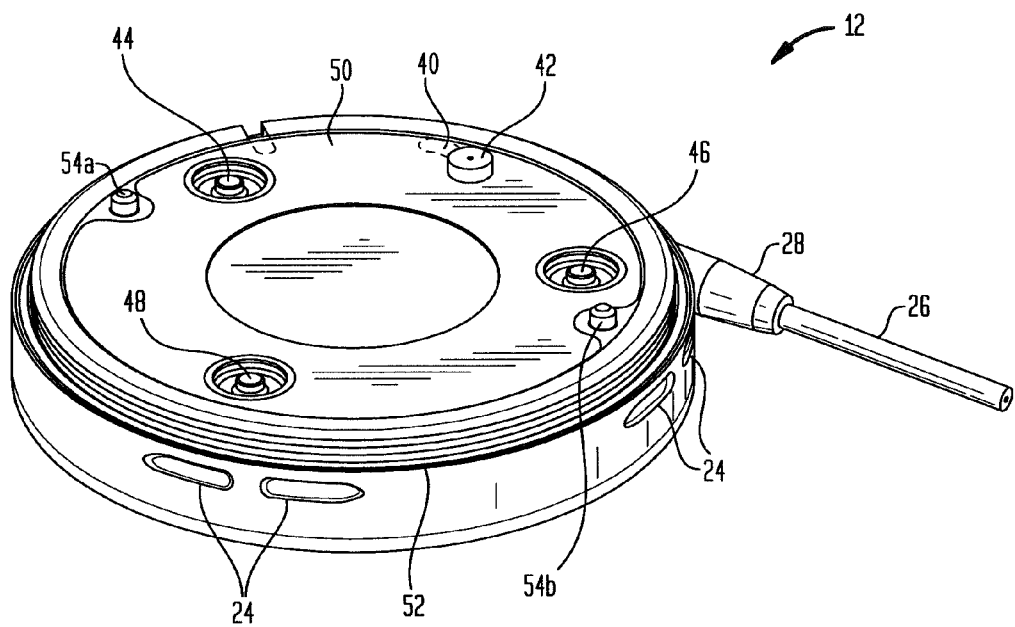
FIG. 9 is a perspective view of a constant flow module assembly of the programmable implantable pump shown in FIG. 1.
Figure 10:
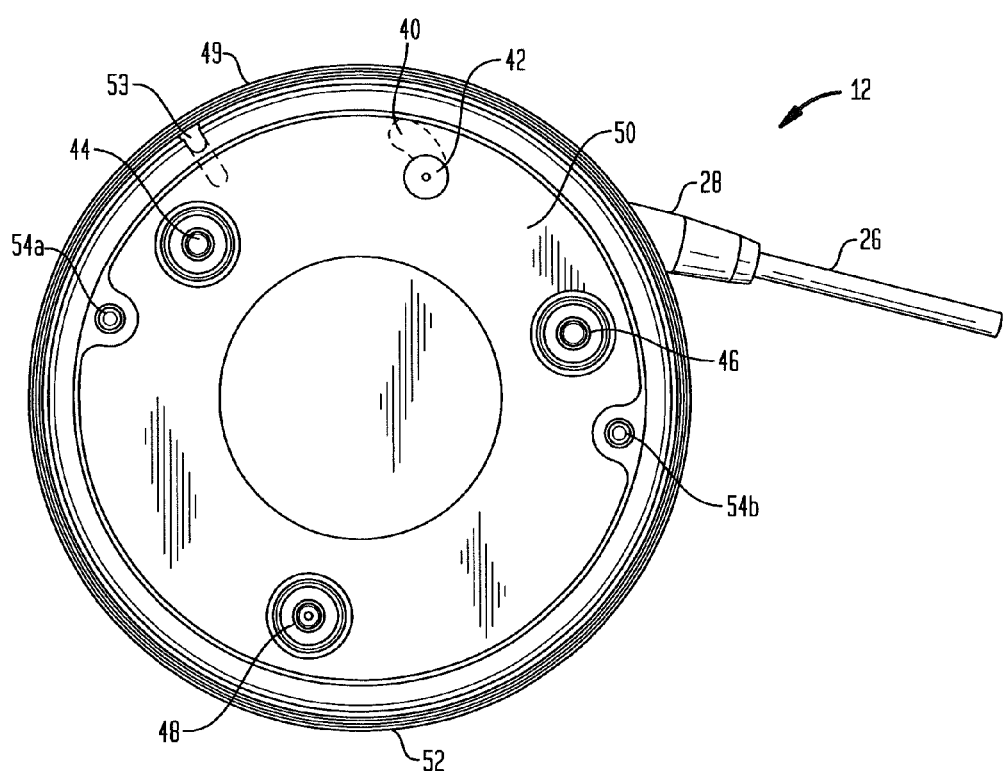
FIG. 10 is a top view of the constant flow module assembly shown in FIG. 9.
Figure 11:
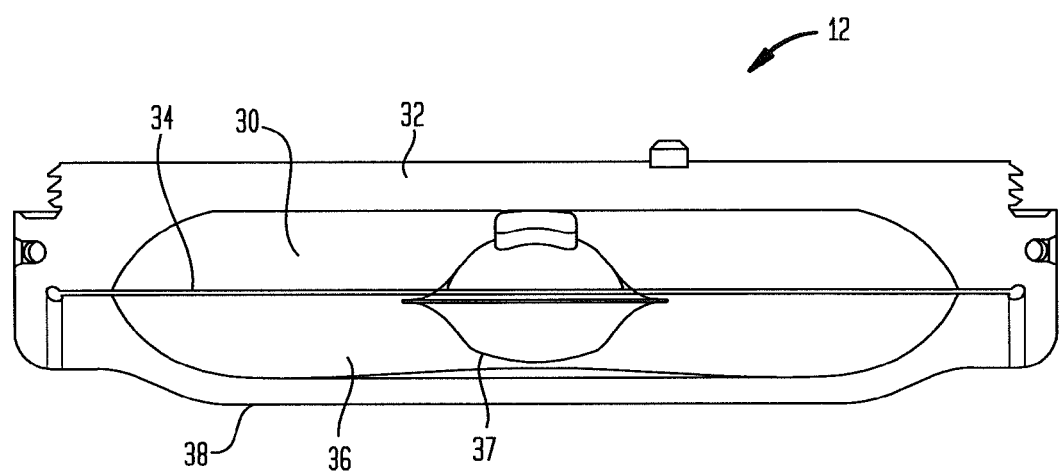
FIG. 11 is cross-sectional view of the constant flow module assembly taken along line AA of FIG. 10.

In constructing pump 10, control module assembly 18 is placed on top of constant flow module assembly 12, and union nut 16 is threaded onto a threaded portion 20 of the constant flow module (best shown in FIGS. 9-11). A flange 22 formed on control module assembly 18 (best shown in FIGS. 12 and 13) allows for the control module assembly to be captured by the union nut 16 and thusly fixably attached to constant flow module assembly 12. A gasket or the like (shown as element 50 in FIGS. 9 and 10) may be placed between constant flow module 12 and control module assembly 18 so as to ensure a sealed fluid connection between the various corresponding ports of those two components (discussed more fully below). Finally, enclosure top 14 is preferably snapped over the construct to form pump 10 as shown in FIGS. 1-7.

As is also shown in FIGS. 1-7 (as well as other figures), pump 10 also includes suture apertures 24 and a fixed catheter 26, both on the constant flow module assembly 12. The former are useful in fixing pump 10 within a patient's body, while the latter is preferably connectable with a longer, and in some cases more flexible, catheter that extends further within the patient's body. Fixed catheter 26 preferably includes a strain relief 28 for reducing stresses and strains at or near the connection between catheter 26 and constant flow module assembly 12. Such strain relief can be of any design as are known in the art, and in the embodiment shown, strain relief 28 is designed to slide over catheter 26 and connect with a portion of constant flow module 12.

The constant flow module operates in much of the same fashion as in previous pumps, including those taught in the aforementioned '892 Patent, as well as in other commonly owned patents such as U.S. Pat. Nos. 4,969,873, 5,085,656, 5,336,194, 5,836,915, 5,722,957, 5,814,019, 5,766,150 and 6,730,060, the disclosures of which are hereby incorporated by reference herein. Essentially, and as is shown more particularly in the cross-sectional view of FIG. 11, constant flow module assembly 12 includes a medication chamber 30 defined by an upper portion 32 of the constant flow module and a flexible membrane 34, and a propellant chamber 36 defined by membrane 34 and a lower portion 38 of the constant flow module. Like in other pump designs, propellant chamber 36 may in actuality be defined as a propellant pillow consisting of membrane 34 and a lower membrane 34A (not shown). As shown in FIG. 11, propellant chamber 36 is preferably filled utilizing a propellant pillow 37, such as that taught U.S. Pat. No. 5,766,150 or U.S. patent application Ser. No. 12/947,187, the disclosures of which are hereby incorporated by reference herein. As is also shown in FIG. 11, upper portion 32 and lower portion 38 of the constant flow module assembly 12 are preferably screwed together, thereby capturing membrane 34 (and membrane 34A) therebetween. Of course, in other embodiments, other connection means may be employed.

As best shown in FIGS. 9 and 10, constant flow module assembly 12 further includes a catheter access opening 40 through which a portion (e.g., a shoulder shown as a portion of below-discussed gasket 50) 42 of catheter 26 extends, a structure 44, an exit 46, and an entrance/exit 48. More particularly, opening 40 acts to both allow direct injection of fluid through catheter 26 and to accept fluid dispelled from control module assembly 18 (as will be discussed more fully below). Structure 44 preferably aids in creating a sealable connection between constant flow module assembly 12 and control module assembly 18 by creating a symmetrical upper surface of assembly 12, thereby evenly spreading compression of a gasket (discussed below) between the two assemblies. Second exit 46 provides fluid to control module assembly 18 to be routed through a valve assembly (also discussed more fully below). Entrance/exit 48 allows for both medication to be injected into chamber 30 and a pressure reading to be taken by a pressure sensor (also discussed more fully below). Assembly 12 also includes a notch 49.

FIGS. 9 and 10 also depict component gasket 50 and circumferential antenna 52. With regard to the former, the gasket is shown as a thin circular portion of silicone or the like which acts to seal around the various openings in flow module assembly 12. Likewise, circumferential antenna 52 is shown as a circular component that fits over threaded portion 20 of the constant flow module and on top of a shoulder formed in the module. This shoulder is better shown in FIG. 11. The antenna is particularly useful in receiving signals emitted from a secondary device during operation of the pump. Circumferential antenna 52 includes a tab 53 which extends into notch 49 so as to be capable of cooperating with control module assembly 18, as will be discussed more fully below. Finally, constant flow module 12 also includes union pins 54a and 54b for engagement with control module 18.

Figure 12:
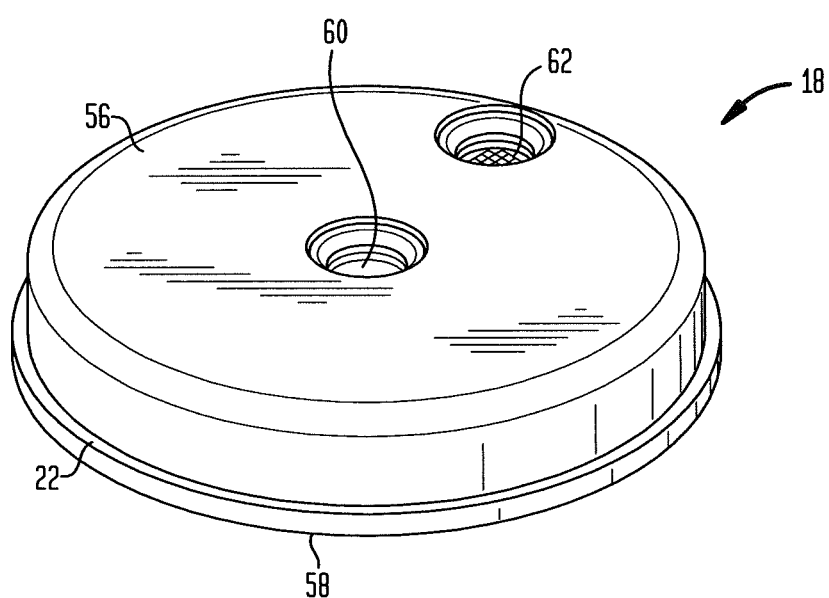
FIG. 12 is a perspective view of a control module assembly of the programmable implantable pump shown in FIG. 1.
Figure 13:
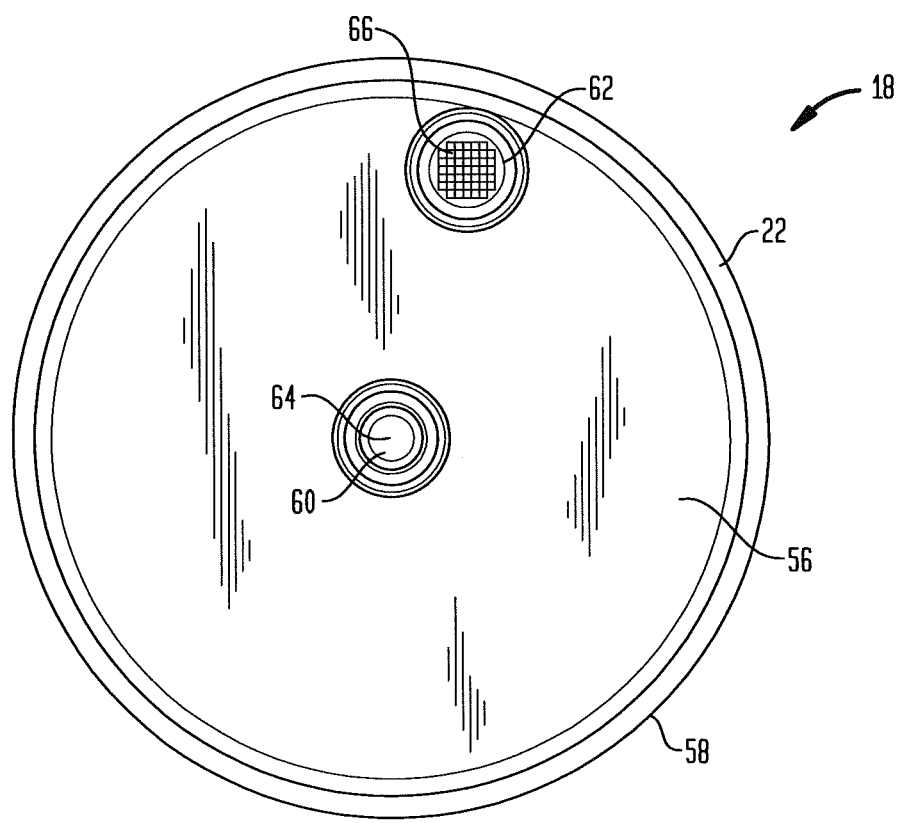
FIG. 13 is a top view of the control module assembly shown in FIG. 12.
Figure 14:
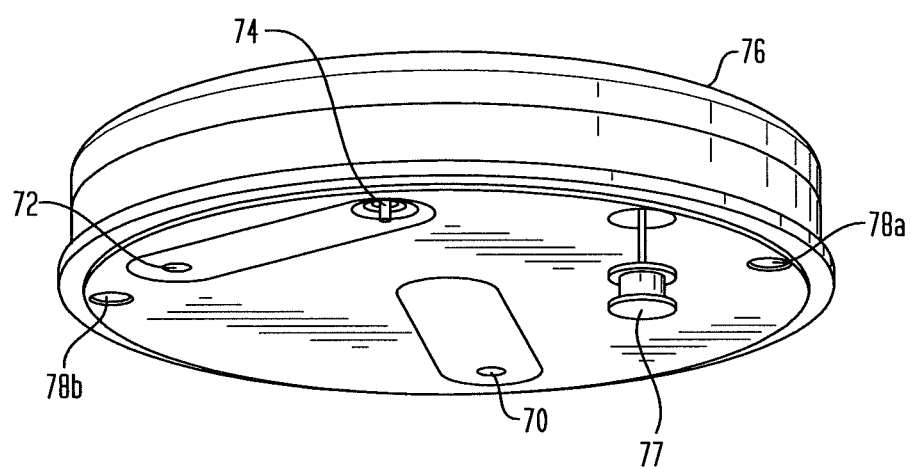
FIG. 14 is a bottom view of the control module assembly shown in FIG. 12.

Turning now to FIGS. 12-14, a fully constructed control module assembly 18 is depicted. The module includes two titanium outer portions, namely, upper portion 56 and lower portion 58. above-discussed flange 22 is formed on lower portion 58. A refill aperture 60 is formed through the center of upper portion 56. A catheter access aperture 62 is formed offset from refill aperture 60. As best shown in FIG. 13, refill aperture 60 allows for a needle to pierce a central septum 64, while catheter access aperture 62 allows for a needle to engage screen member 66. It is to be understood that screen member 66 is designed with a plurality of apertures that are sized so as to prevent needles having a certain size from extending therethrough. This allows for larger needles to be designated for a refill procedure (through central septum 64), while smaller needles are provided for catheter direct access. This is an added safety measure, that is discussed in application Ser. No. 13/276,469 entitled "Mesh Protection System," and screen member 66 is similar to the like structure formed in that application.

FIG. 14 depicts a view of lower portion 58 of module 18. As shown, lower portion 58 includes several openings, including refill opening 70, reception opening 72, exit opening 74 and electronic access opening 76. An alternate embodiment antenna assembly 77 is shown removed from within electronic access opening 76, but with wires that attach the antenna to the module depicted. It is to be understood that pump 10 can utilize either antenna assembly depicted in the present application, both antenna assemblies, or an alternate assembly not shown herein. Moreover, union pin reception openings 78a and 78b are provided for receiving union pins, 54a and 54b, respectively. Refill opening 70 serves two purposes, namely, allowing for fluid injected through refill aperture 60 to pass into chamber 30 through entrance/exit opening 48, and allowing for access (as will be discussed below) to a pressure sensor disposed within module 18. Reception opening 72 allows for fluid dispelled from exit 46 of constant flow module 12 to be introduced into a valve assembly disposed within module 18. Exit opening 74 overlies opening 40 and shoulder 42 of constant flow module 12 in a fully assembled state. This allows for fluid ultimately dispelled from the valve assembly included within module 18 to flow through catheter 26, and thusly to the patient. Finally, electronic access opening 76 provides a corridor for certain internal electronic structures discussed below to communicate with tab 53 of antenna 52.

Figure 15:
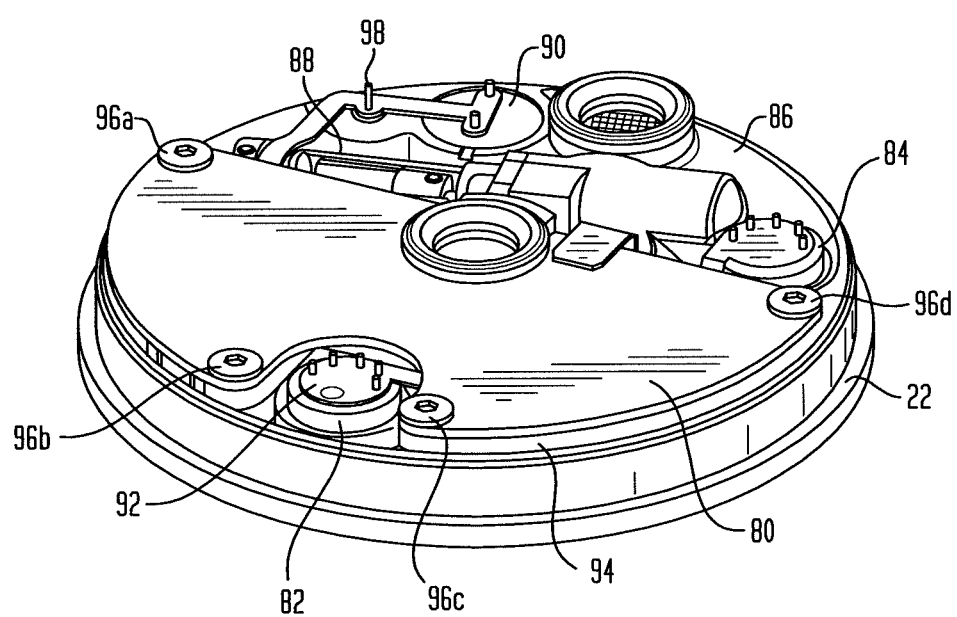
FIG. 15 is a perspective view of the control module assembly shown in FIG. 12, with a titanium enclosure top removed therefrom.
Figure 16:
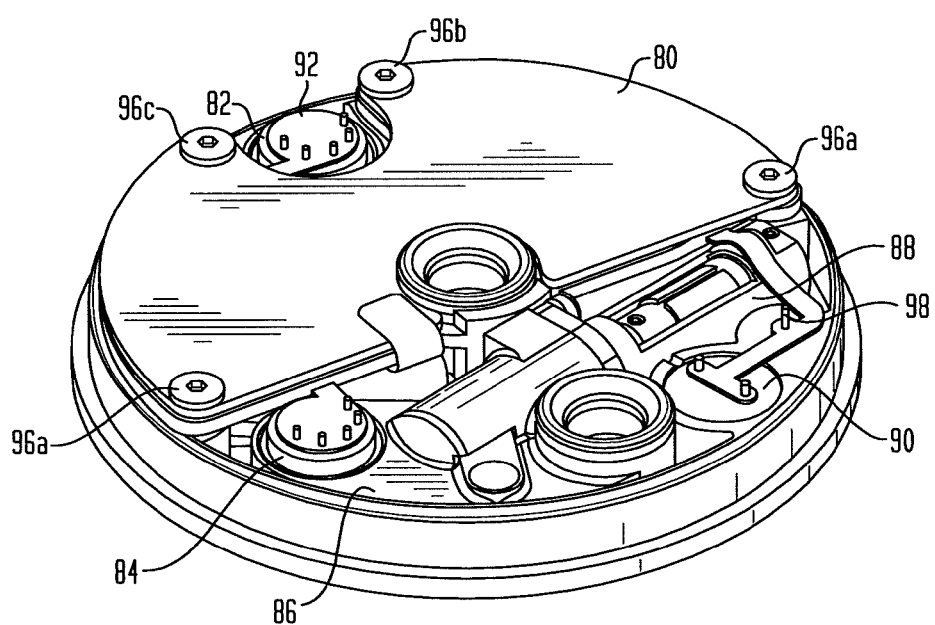
FIG. 16 is another perspective view similar to that shown in FIG. 15.
Figure 17:
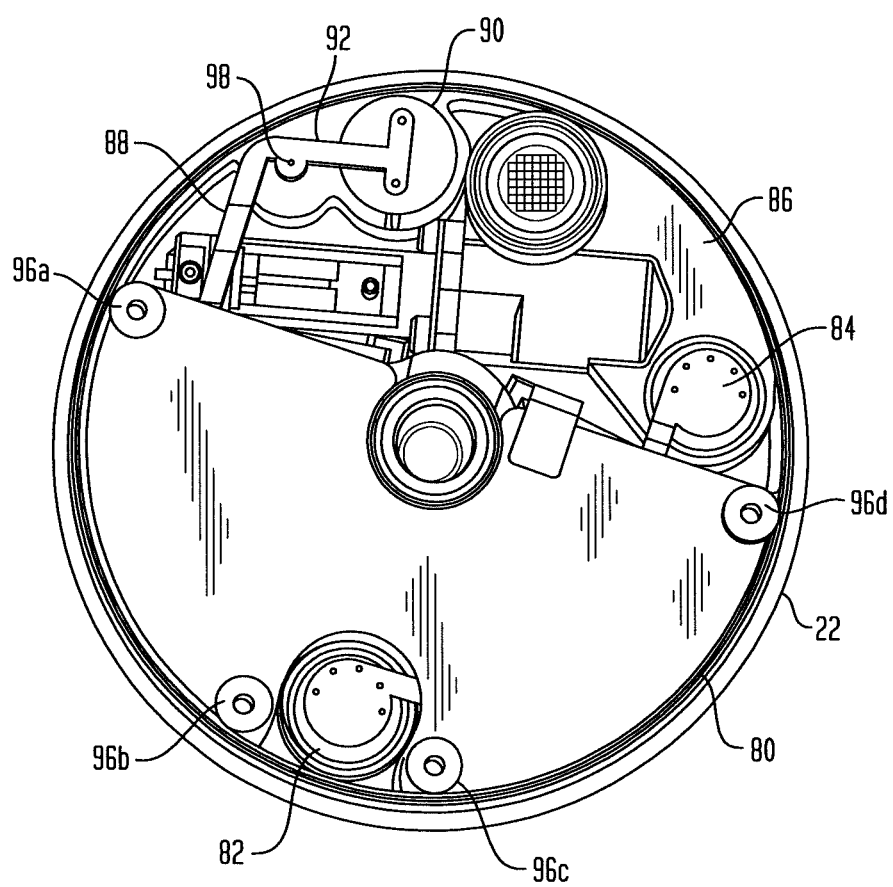
FIG. 17 is a top view of the control module assembly shown in FIGS. 15 and 16.

FIGS. 15-17 depict module 18 with upper portion 56 removed therefrom. As shown, within its interior, module 18 includes a circuit board 80, a first pressure sensor 82, a second pressure sensor 84, a valve block 86, a motor assembly 88, a buzzer 90, and a flexible conductive element 92. FIGS. and 17 depict similar views to FIG. 15, albeit from different perspectives. Circuit board 80 is held to a circuit board support 94, which is better shown in FIG. 18 where circuit board 80 is removed. Screws 96a-96d hold circuit board 80 to circuit board support 94. Flexible conductive element 92 preferably provides electrical interconnection among circuit board 80, first pressure sensor 82, second pressure sensor 84, motor assembly 88 and buzzer 90. Module further includes a feed through 98, which is also preferably connected with flexible conductive element 92, and which extends through electronic access opening 76 on the bottom of module 18. This element preferably provides the interconnection of the internals of module 18 with antenna 52, specifically tab 53.

Figure 18:
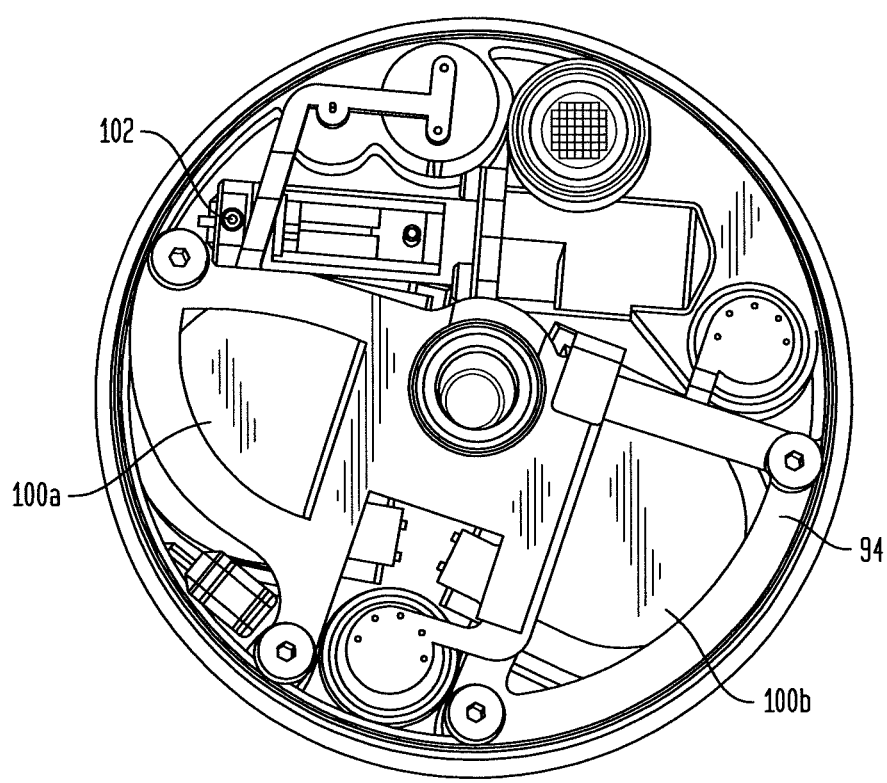
FIG. 18 is another view of the control module assembly shown in FIGS. 15-17, with an additional portion removed therefrom.
Figure 19:
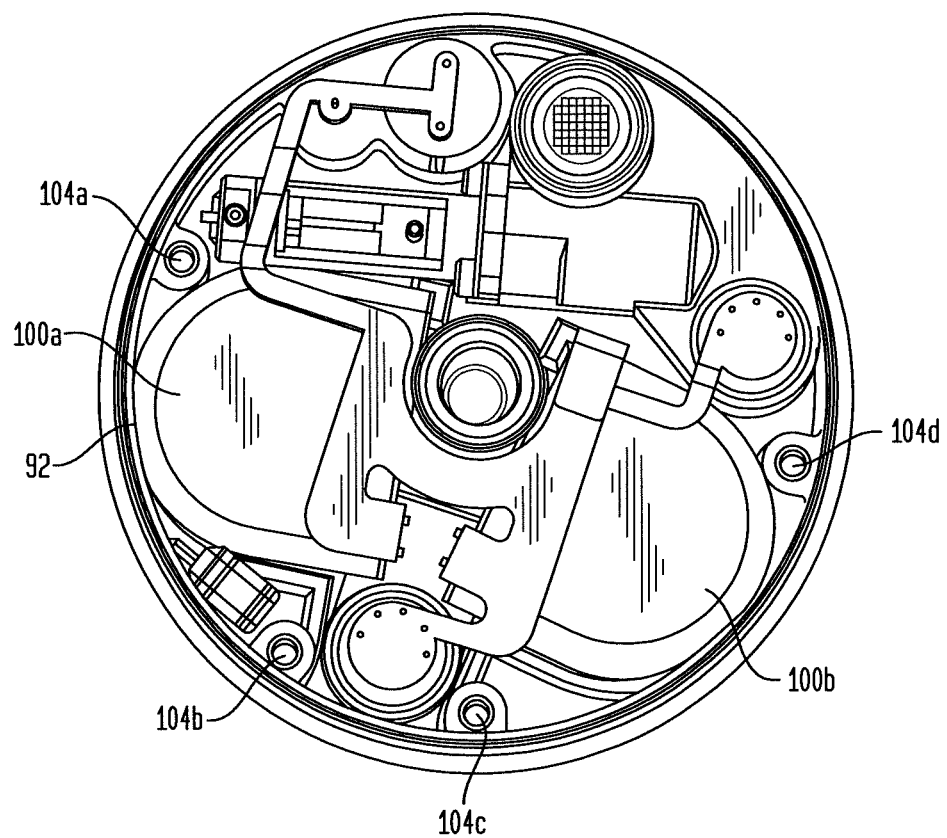
FIG. 19 is a top view of the control module assembly shown in FIG. 18, with a further additional portion removed therefrom.

As noted above, FIG. 18 depicts the internals of module 18 with circuit board 80 removed therefrom. In this view, it is shown that module 18 also includes batteries 100a and 100b for powering the pump. Also shown, is the interconnection among flexible conductive element and flexible conductive element 92 and both batteries. FIG. 19 shows the internal structure of module 18, this time with circuit board support 94 removed therefrom. In this figure, the configuration and interconnection among the elements and flexible conductive element 92 are further depicted. In the embodiments shown, flexible conductive element is constructed of a polymide material, but can be any other conductive element, including wires or the like. Also more clearly shown in FIGS. 18 and 19 is the connection between motor assembly 88 and lower portion 58. Specifically, a set screw 102 is provided at one end of the motor assembly and threaded into a portion of lower portion 58. Moreover, FIG. 19 shows apertures 104a-d, which are designed to accept screws 96a-96d, respectively. Thus, circuit board is held tightly not only to circuit board support 94, but also lower portion 58.

Figure 20:
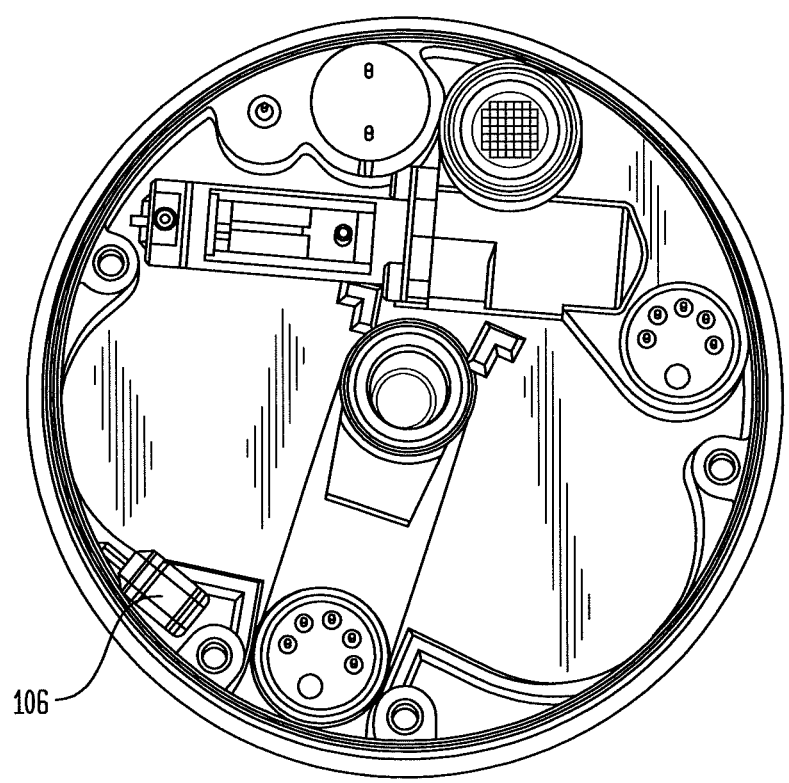
FIG. 20 is a top view of the control module assembly shown in FIG. 19, with an even further additional portion removed therefrom.

FIG. 20 depicts module 18 in a similar view to that of FIG. 19, but with flexible conductive element 92 and batteries 100a and 100b being removed therefrom. In this view, a capacitor 106 is shown. This component allows for the generation of higher voltage than batteries 100a and 100b themselves. In general, capacitor 106 operates like a standard capacitor, storing charge for use in powering the pump. It is to be understood that capacitor 106 could be removed depending upon the particular batteries that are utilized. For instance, batteries that generate higher voltages and less current typically will negate the need for a capacitor. However, batteries suitable for inclusion in module 18 tend to be produced in the lower voltage range (3.2V-3.8V). Moreover, smaller capacitors could be included on circuit board 80 to achieve the same goal as capacitor 106.

Figure 26:
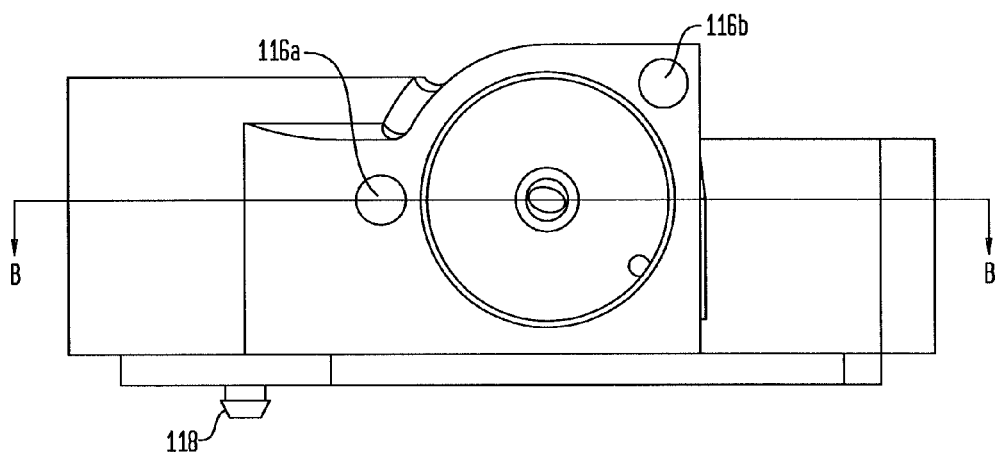
FIG. 26 is a left side view of the valve block shown in FIG. 25.
Figure 27:
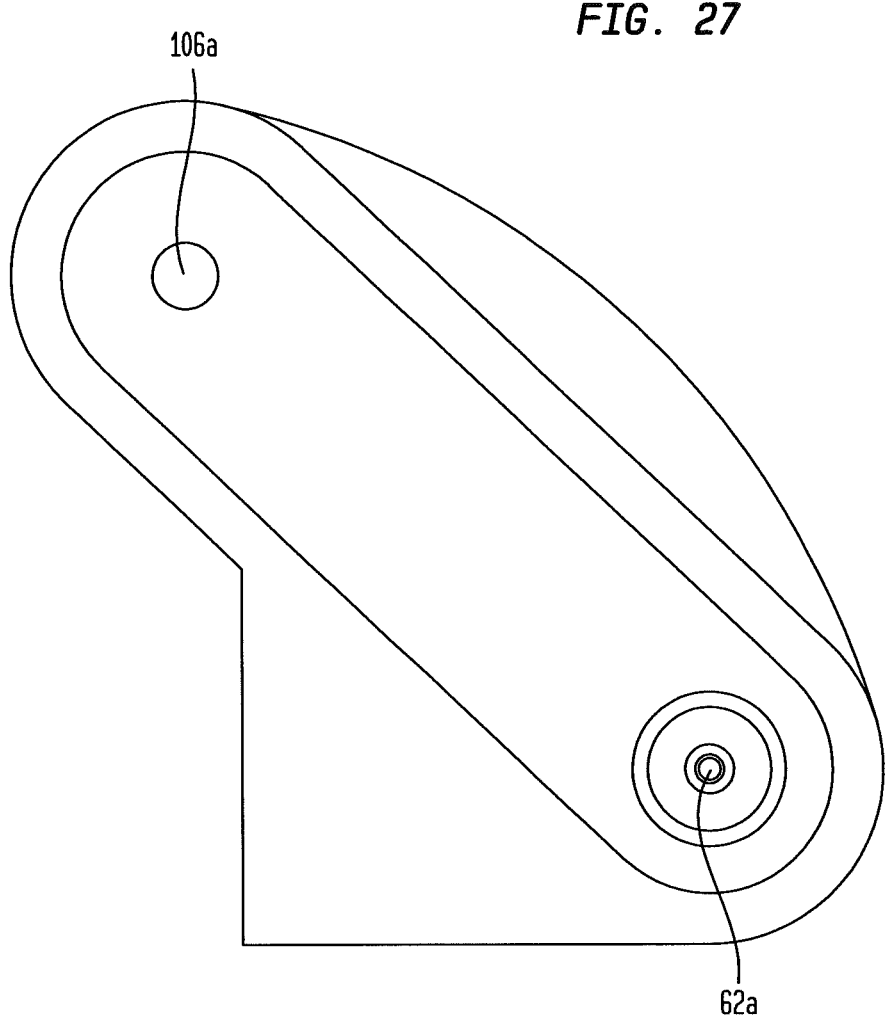
FIG. 27 is a bottom view of the valve block shown in FIG. 25.
Figure 28:
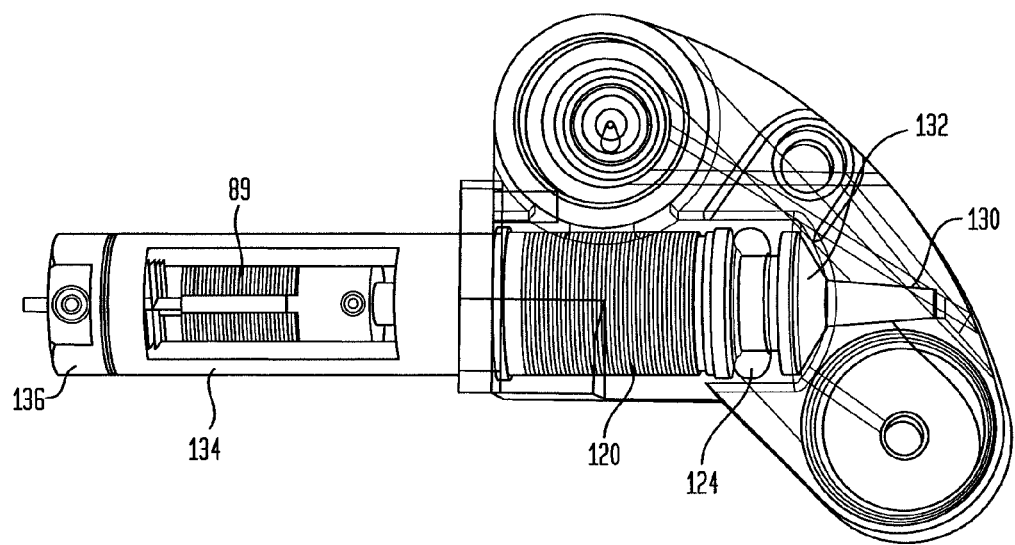
FIG. 28 is a view similar to that shown in FIG. 21, with the valve block shown in phantom.

FIGS. 21 and 25-29 focus on valve block 86, its internal components, and its cooperation with motor assembly 88. As shown, valve block 86 includes a pressure sensor receiving aperture 106, as well as catheter access aperture 62. Pressure sensor receiving aperture 106 is designed to receive second pressure sensor 84, as well as allow for fluid to come into contact with that pressure sensor. Valve block 86 also includes a first body portion 108 and a second body portion 110. First body portion 108 includes apertures 62 and 106, as well as several fluid passageways and a valve receiving channel (best shown in FIG. 28) for allowing fluid flow within the valve block and ultimately to the patient. Second body portion 110 is essentially a hollow cylindrical body, the interior of which is designed to receive a portion of the valve. This again is best shown in FIG. 28, with FIG. 26 depicting a front view of same. It is noted that valve block 86 is depicted by itself in FIGS. 25-27, with FIG. 27 depicting a bottom surface thereof. As shown in that drawing, apertures 62a and 106a cooperate with the above discussed apertures 62 and 106, respectively.

Figure 21:
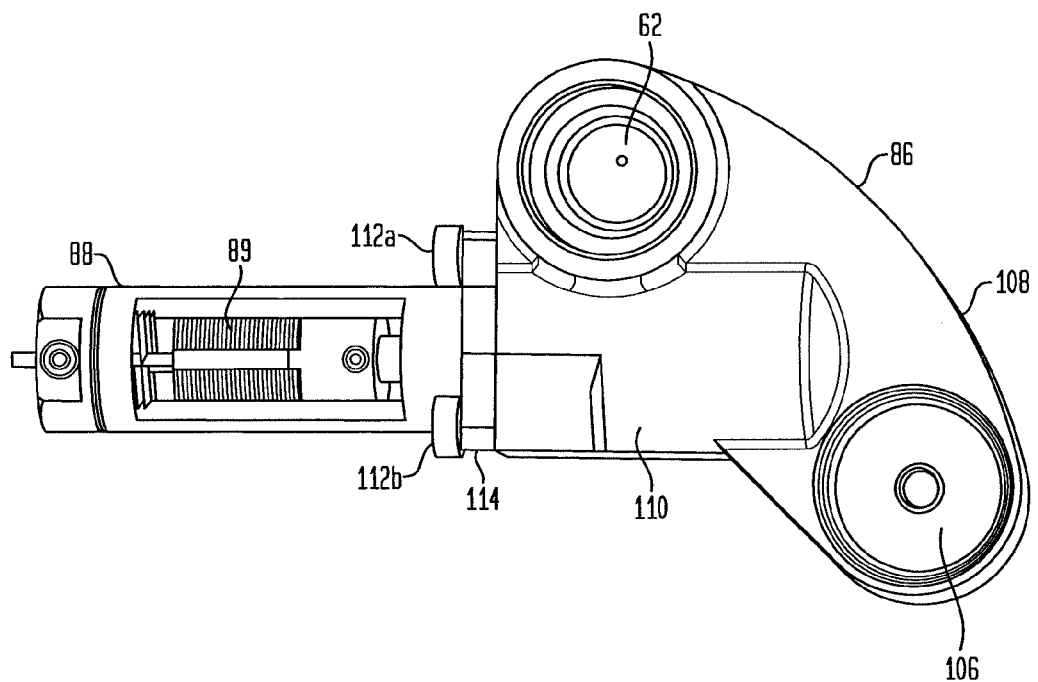
FIG. 21 is a top view of a motor and valve block assembly included in the control module assembly shown in FIG. 12.

As also shown in FIG. 21, motor assembly 88 is connected with valve block 86 by two screws 112a and 112b, which extend through apertures in a flange portion 114 of the motor assembly, and into apertures 116a and 116b, respectively, of the valve block (best shown in FIG. 26). This cooperation fixably connects motor assembly 88 with valve body 86. As noted above, motor assembly 88 is also connected to module 18 via set screw 102. Likewise, valve block 86 is connected to other portions of module 18 via pin 118, as best shown in FIG. 26. That pin preferably includes a bulbous head portion that, once inserted within a hole in module 18, acts to prevents removal of the valve block.

Figure 22:
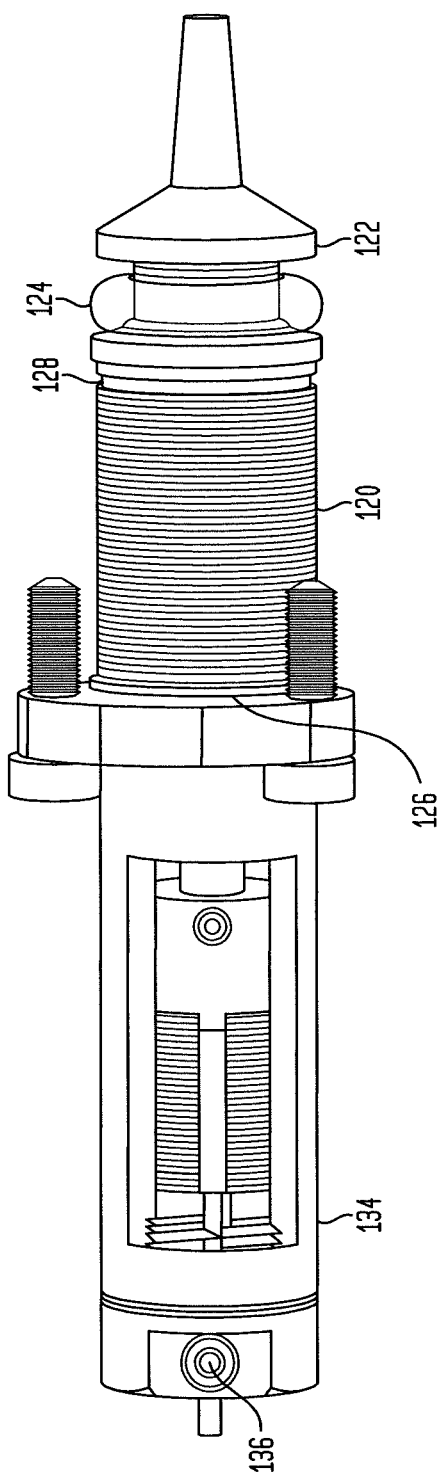
FIG. 22 is a top view of a motor, bushing, and valve assembly included in the construct shown in FIG. 21.
Figure 23:
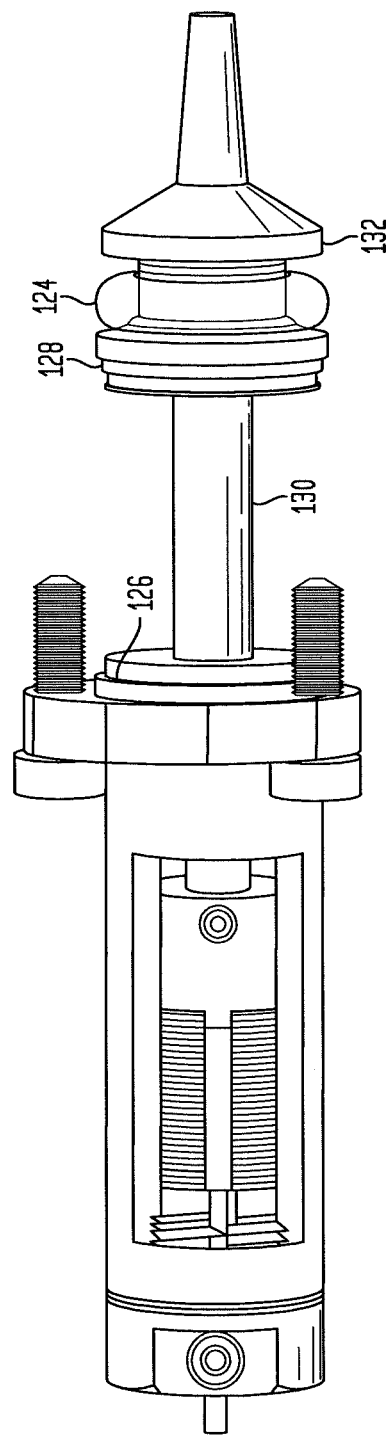
FIG. 23 is a top view of the assembly shown in FIG. 22 with the bellows removed therefrom.
Figure 24:
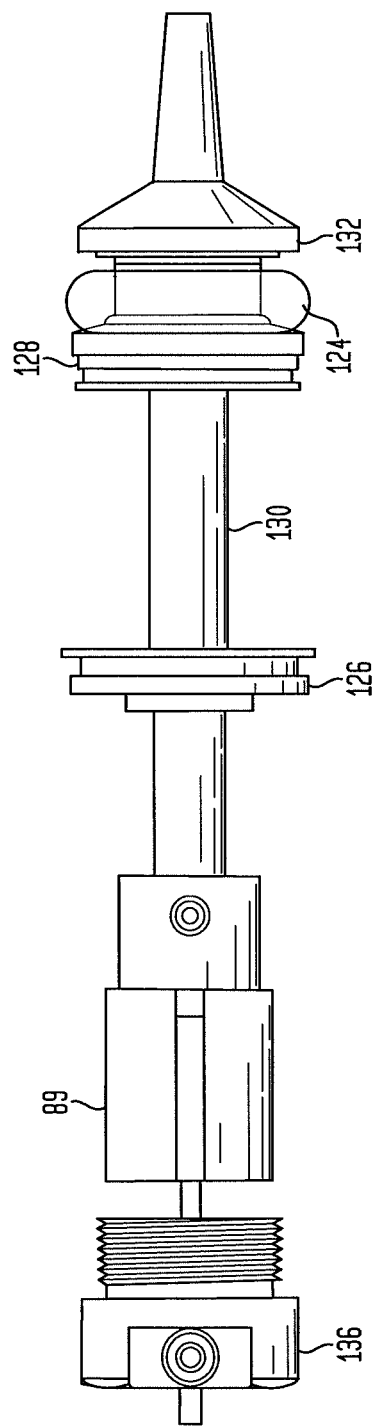
FIG. 24 is a view similar to that of FIG. 23, with a stem bushing construct removed therefrom.
Figure 25:
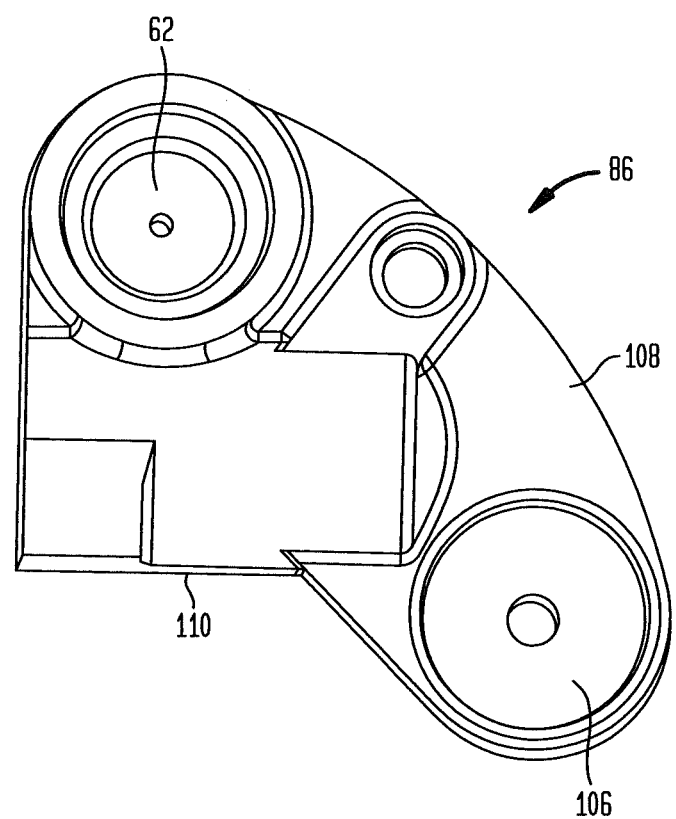
FIG. 25 is a top view of the valve block depicted in FIG. 21.

FIG. 22 depicts motor assembly 88 without valve body 86, and highlights the portions of the assembly that extend into the valve body. Specifically, motor assembly 88 includes a bellows 120, valve 122, and an o-ring 124. Bellows 120 is preferably welded to weld ring 126, which in turn is welded to flange 114. Likewise, bellows 120 is preferably welded to valve at surface 128. Referring now to FIG. 23, in which bellows 120 is removed, it is shown that valve 122 consists of a valve stem 130 which extends through a valve bushing 132. It is around this valve bushing that o ring 124 is disposed. Valve stem 130 includes at a distal end a tapered portion. FIG. 24 on the other hand depicts the assembly with a motor housing 134 removed therefrom. In this view, weld ring 126 is clearly shown. Also shown is a motor mount plug 136 which screwably connects with motor housing 134.

Figure 29:
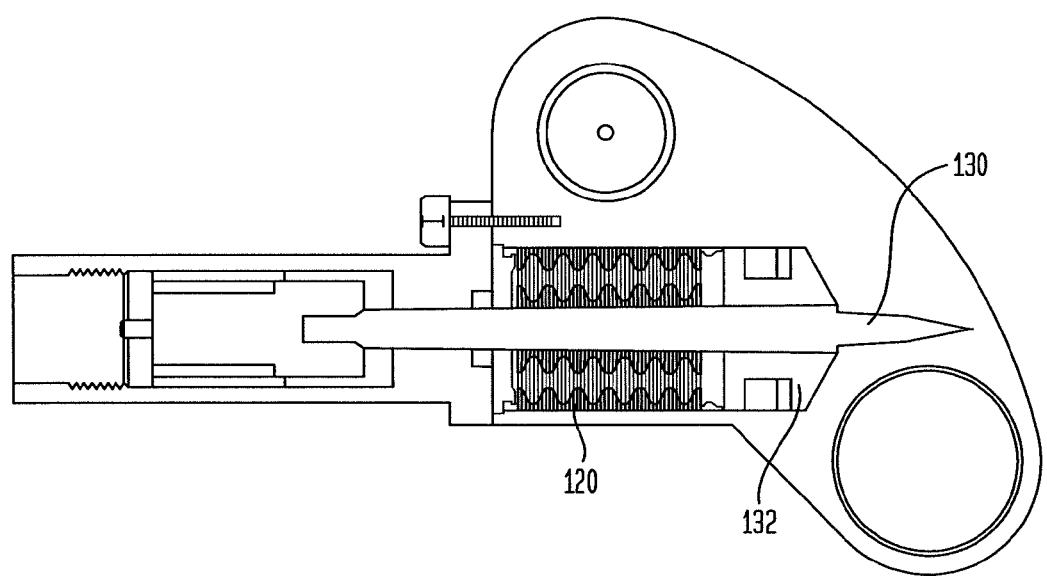
FIG. 29 is a cross-sectional view taken along line BB of FIG. 26.

Motor 89 of motor assembly 88 is preferably a piezoelectric motor, as such a motor does not include a permanent magnet, which makes the motor MRI compatible. In addition, piezoelectric motors are generally of a smaller size and require less energy for operation. Still further, piezoelectric motors operate in a straight line, which is ideal in the present instance, as will be discussed below. However, it is to be understood that motor 89 could be other types of motors, including stepper motors or the like. Of course, certain of the above-mentioned benefits of the piezoelectric motor may not be met by such alternate motor designs. Operation of motor 89 imparts a force upon valve stem 130, which moves within second body portion 110 of valve block 86. The combination of bellows 120 and o ring 124 insures that any fluid flowing within valve block 186 cannot seep outside of that component. In other words, bellows 120 and o-ring 124 insure a sealable connection between motor assembly 88 and valve block 86. As is shown in FIGS. 28 and 29, the most distal portion of valve stem 130 extends within the fluid flow path, and the conical nature of that distal portion provides that movement of the valve stem results in greater or lesser fluid flow threw valve block 86. The inclusion of a stepper motor such as the one discussed above insures that fine adjustments of flow rate through the valve block can be realized. In fact, movement of the valve relates in a linear or near linear fashion to the flow rate. The above-discussed sealable nature of bellows 120 and o ring 24 insures hermetic sealing within the valve block, and thusly prevents fluid from flowing anywhere other than the valve block. This is particularly important given the other components of module 18.

In the embodiment shown, valve stem 130 and valve portion 132 are shown as constructed of titanium material. It is to be understood that any suitable material may be employed. Moreover, it is to be understand that valve stem 130, at its most distal end, could include a silicon covering or the like in order to insure a full closure of the valve if desired. Likewise, while o ring 124 as shown as being constructed of a silicon material, any other suitable material may be employed. For instance, Teflon may be employed, as can a material known as PORON®.

In operation, fluid dispelled from chamber 30 (under pressure provided by chamber 36) travels through both exits 46 and 48. The fluid dispelled through exit 48 is preferably directed into contact with first pressure sensor 82, so a pressure reading of the fluid within chamber 30 can be taken. The fluid dispelled through exit 46 preferably first travels through a filter and capillary construction, as are known in the art. In one example of such a structure, a filter and capillary are coiled around an underside of upper portion 32. Fluid flows through the filter, which is designed to prevent particulates and other undesirable matter of flowing into the capillary, and thereafter flows through the capillary, which is essentially a very small tube with a small diameter that allows a maximum flow rate of fluid therethrough. That fluid then flows through aperture 106a and into the passages provided in valve block 86. Second pressure sensor 84 takes a pressure reading of the fluid within the valve block.

Once within valve block 86, the fluid flows into contact with the distal end of valve stem 130. Depending upon the positioning of the valve stem, the flow of the fluid will either be reduced or remain the same as the maximum flow rate dictated by the aforementioned capillary. Second pressure sensor 84 is positioned to take a reading of the pressure before the valve portion, and thusly the comparison of the readings taken by first pressure sensor 82 and second pressure sensor 84 can be utilized to determine the actual flow rate of the fluid after passing through the resistor and the valve. This is preferably determined by circuit board 80, as sensors and 84 are electrically connected thereto by flexible conductive element 92. If the flow rate is not desired, motor 89 can be operated to vary the position of valve stem 130. Subsequent to contacting the valve, fluid flows through other passages formed in valve block 86, through aperture 62a and ultimately through catheter 26. Depending upon the placement of the catheter within the patient, the fluid is delivered to the desired portion of the patient in which the catheter is directed.

It is to be understood that pump 10 preferably operates with little outside interaction required. Aside from refilling chamber 30 with an active substance, a doctor or other medical professional likely only needs to interact with the pump in order to set a desired flow rate. This may be accomplished through the use of a wand or other transmitter/receiver (not shown) that interfaces with antenna 92. Once the flow rate is set, pump 10 preferably operates on its own to maintain the flow rate. Pump 10 may also be programmed to provide different flow rates at different times of the day. For instance, patients may require lesser doses of medication while sleeping, and heavier doses of medication upon waking up. Circuit board 80 can be designed to allow for such programming. Above-noted buzzer 90 is designed to emit an audible warning upon certain conditions, including low battery, low fluid level within chamber 30, low or high temperature conditions, and high pressure, which may indicate overfilling of chamber 30, low pressure differential across the resistor capillary or blockage within catheter 26. Upon recognizing the audible sound, the patient can contact his or her medical professional.

Valve 122 may also include a positioning sensor (not shown) or the like associated therewith. Such a sensor may be capable of providing information relating to the positioning of the valve to circuit board 80. Such positioning sensors can include many different designs. For example, light reflective technology can be employed to determine at any given moment the position of the valve. Likewise, valve 122 may be provided with one or more conductive elements that interact with conductive elements provided on or near valve block 86. The completion of an electrical circuit in such a case can indicate the positioning of valve 122. Still further, the positioning sensor can take the form of an induction coil capable of determining the positioning of the valve therein. A slide potentiometer may also be employed, as can a stack switch.

During a refill procedure, pump 10 can be monitored through the use of the wand or other transmitter/receiver. A computer program associated with such device and pump 10 can indicate to the doctor whether the refill needle is correctly placed within the pump. Known problems with refilling implantable pumps are misapplications of a refill needle to the tissue of the patient (so called pocket fills) and to a bolus opening such as catheter access aperture 62. Directly injecting a patient with a dose of medication meant for prolonged release from chamber 30 can have dire consequences. During the monitoring of the refill procedure, a quick change in pressure within chamber 30 can be recognized by the medical professional, thereby ensuring placement of the needle within refill aperture 60. This is a significant safety feature in pump 10.

The exterior portions of pump 10 are preferably constructed of PEEK, including constant flow module assembly 12, enclosure top 14 and union nut 16. On the other hand, the exterior portions of control module assembly are constructed of titanium, which ensures the hermetic nature of that component. However, certain interior portions of the module are also constructed of PEEK, including circuit board support 94. While these are indeed the materials utilized in the construction of a preferred pump 10, other materials may be employed in other embodiments. For instance, other polymeric materials may be employed that provide for similar strength, while maintaining the low overall weight provided for by the PEEK material. Likewise, other metallic materials may be substituted for titanium, such as stainless steel or the like. The only limitation is that the materials selected should be bio-compatible to ensure such are not rejected by the patient after implantation.

Several variations of above-discussed pump 10 will now be discussed. It is to be understood that all or some of these variations may be incorporated into an implantable pump according to the present invention. Where possible, like elements to those discussed above are referred with reference numerals in a different 100-series of numbers.

Figure 31:
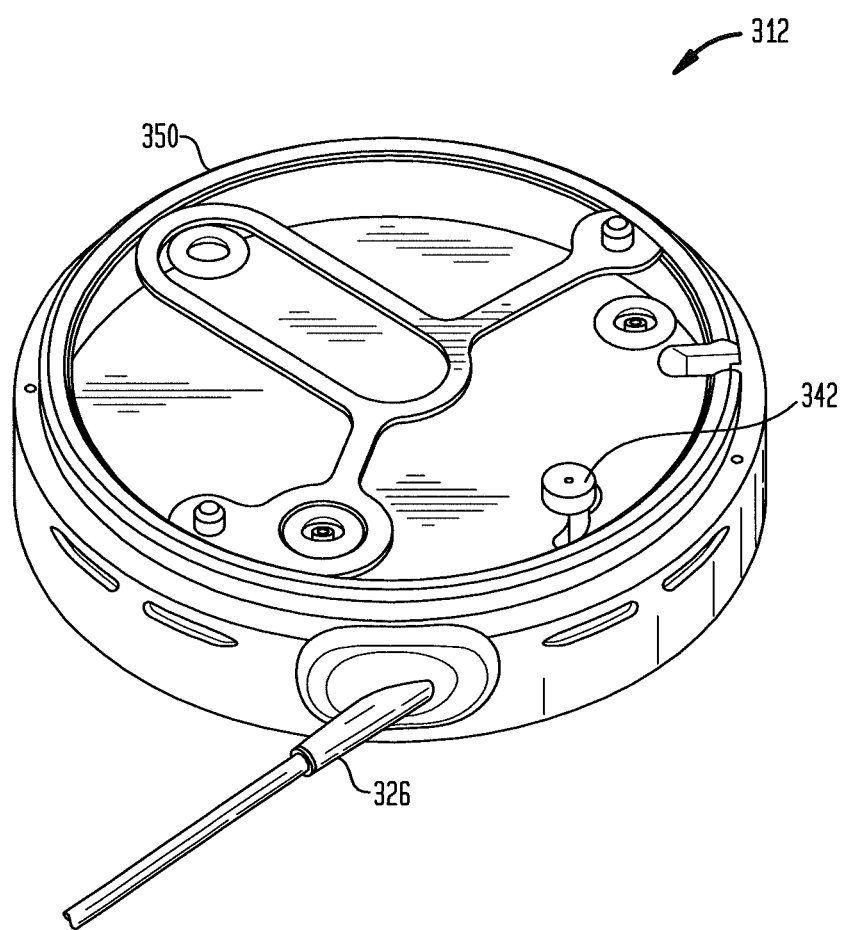
FIG. 31 is a top view of an alternate embodiment constant flow module.
Figure 32:
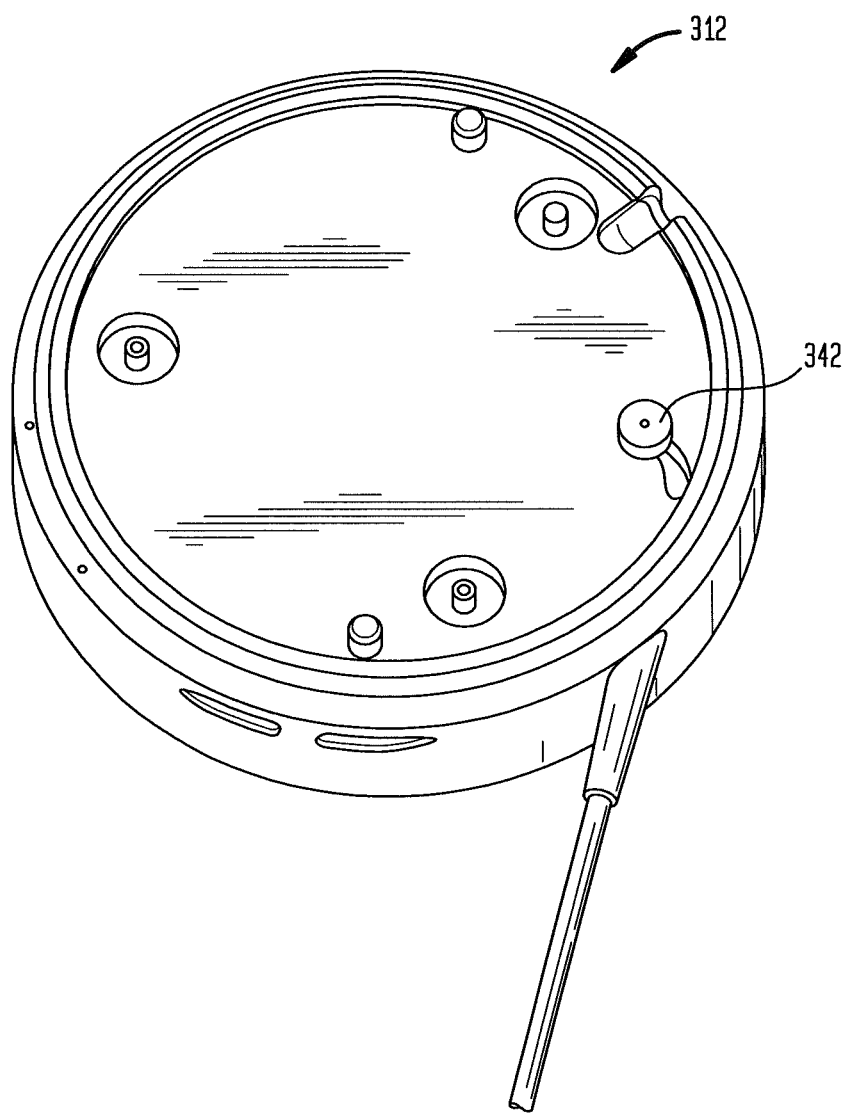
FIG. 32 is a top perspective view of the constant flow module shown in FIG. 31.
Figure 33:
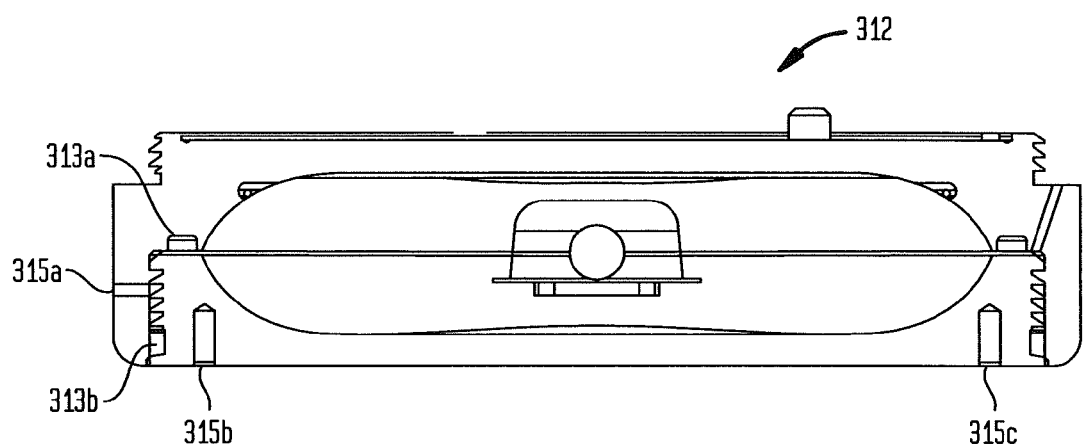
FIG. 33 is a side cross-sectional view of the constant flow module shown in FIG. 31.

For instance, FIG. 31 depicts a top portion of an alternate embodiment constant flow module 312, which includes a differently shaped gasket 350. That gasket has been removed from FIG. 32. In this embodiment, a portion 342 stands alone as part of catheter 326. FIG. 33 depicts a side cross section of constant flow module 312. As is seen in this view, module 312 differs from that of module 12 in that a bottom thereof is no longer contoured, but rather, exhibits a flat configuration. Constant flow module 312 has also been provided with two o-rings 313a and 313b. Where ring 313a ensures a sealing of the propellant and medication chambers of module 312, ring 313b ensures no material can leak from module 312. Still further, module 312 includes holes 315a-c. Hole 315a preferably receives a pin or the like (not shown) that acts to prevent the two housing portions included in module 312 from inadvertently disengaging by preventing unscrewing of those portions. On the other hand, holes 315*b* and 315*c* aid in connecting those portions to each other. Specifically, holes 315*b* and 315*c* are capable of interfacing with a tool for use in screwing the module portions together. Of course, other embodiments may include any number of similar holes.

Figure 34:
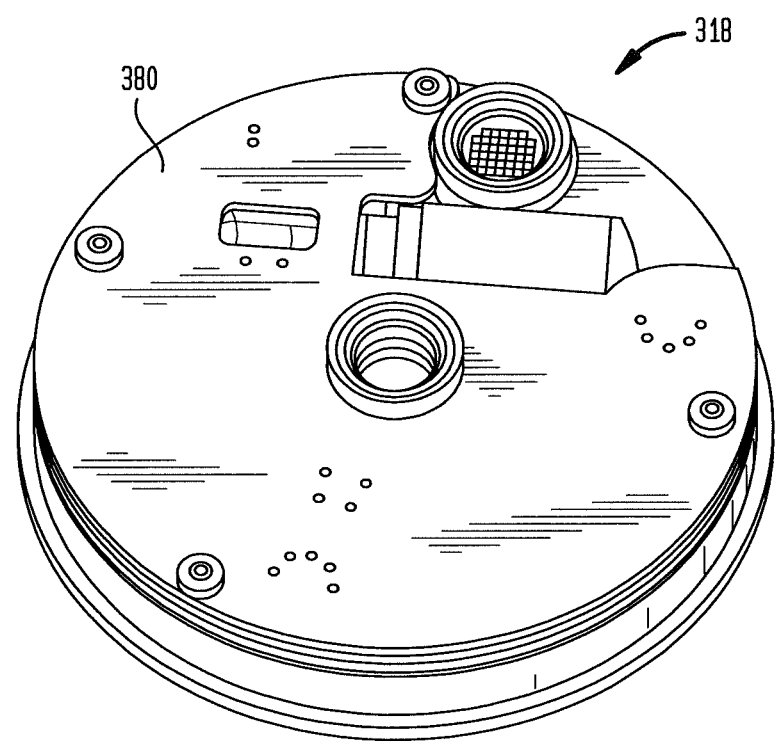
FIG. 34 is a top perspective view of an alternate embodiment control module assembly, with a titanium enclosure top removed therefrom.
Figure 35:
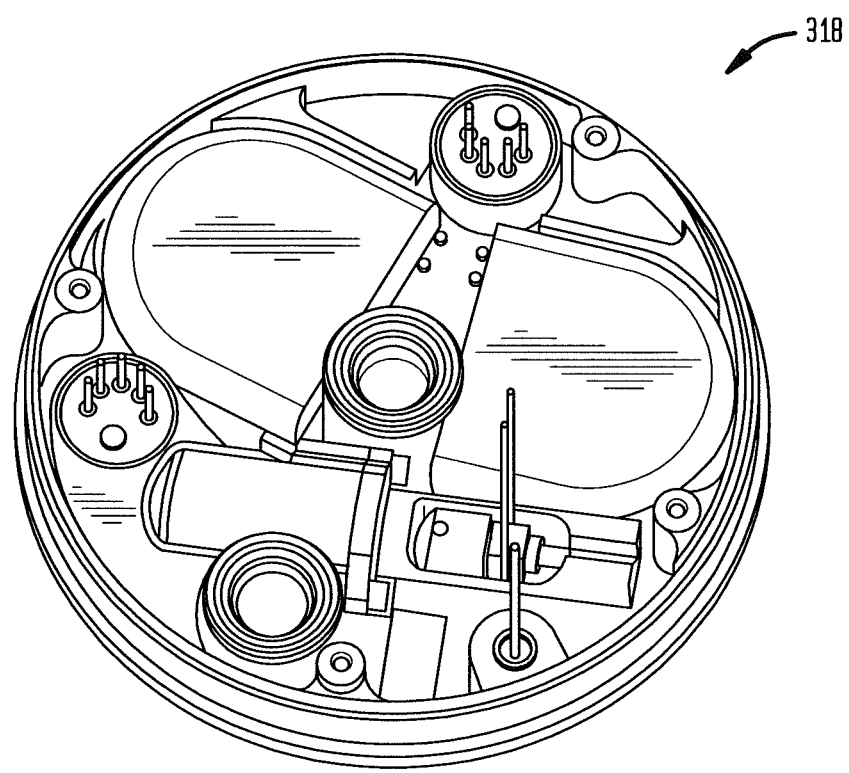
FIG. 35 is another top perspective view of the control module assembly shown in FIG. 34, with a titanium enclosure and circuit board removed therefrom.

FIG. 34 depicts an alternate embodiment control module assembly 318 in which an element similar to the above-discussed flexible conductive element 92 has been eliminated. In this embodiment assembly 318, a circuit board 380 acts to connect all of the electrical elements of the module. FIG. 35 depicts the module 318 with circuit board 380 removed.

Figure 36:
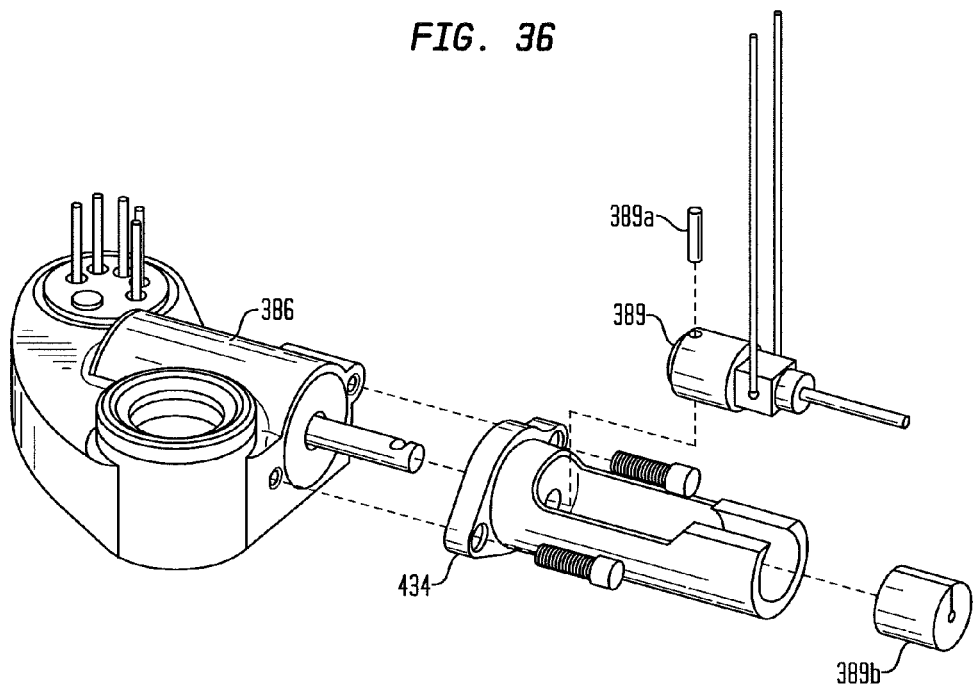
FIG. 36 is an exploded view of an alternate embodiment motor and valve block assembly included in the control module assembly shown in FIG. 34.
Figure 37:
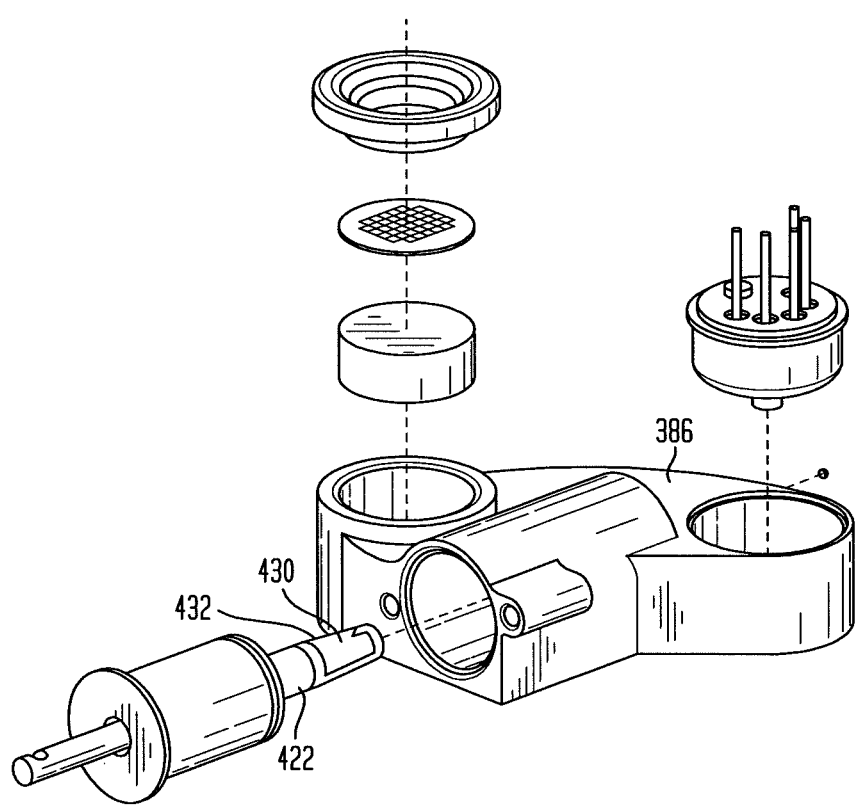
FIG. 37 is another exploded view of the motor and valve block assembly shown in FIG. 34, with certain portions removed therefrom.

FIGS. 36 and 37 depict alternate embodiment valve block 386 and motor assembly 388, as well as the cooperation of those two elements. The major differences between this embodiment and those discussed above lies in several areas. For one, valve 422 includes a valve stem 430, which includes an overmolded silicone valve tip 432. This tip ensures full seating within a valve seat (not shown) located in block 386, as well as allows for fine adjustment of flow rates therethrough. In addition, motor assembly 388 includes a solid housing 434, and does not include a portion similar to plug 136. Finally, motor 389 is held in place by clamp elements 389*a* and 389*b*. Both elements are fitted into or onto different portions of the motor and thereafter affixed to block 386, preferably through the use of epoxy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A programmable pump for dispensing a fluid at varying flow rates to a patient comprising:
a constant flow module including a first chamber housing the fluid, a first opening in fluid communication with the first chamber and a second opening in fluid communication with a catheter; and
a hermetically sealed control module attached to the constant flow module and including a motor assembly and valve block, the valve block being in fluid communication with the first and second openings, the motor assembly having a stepper motor, a valve connected with the stepper motor, and a bellows surrounding a portion of the valve,
wherein the valve is connected to the stepper motor by a valve stem, a distal end of the valve stem being tapered and a distal-most portion of the valve stem extending within a flow path of the fluid, and
wherein the flow rate of the fluid dispelled from the first chamber is affected by varying positioning of the valve.

2. The programmable pump of claim 1, wherein the bellows surrounds and hermetically seals the portion of the valve in all positions of the valve.

3. The programmable pump of claim 2, wherein the bellows is tubular and of varying length.

4. The programmable pump of claim 3, wherein the valve includes a valve bushing and a valve stem extending through the valve bushing.

5. The programmable pump of claim 4, wherein the motor assembly further includes an o-ring surrounding the valve bushing.

6. The programmable pump of claim 1, wherein the constant flow module further includes a second chamber separated from the first chamber by a first flexible membrane.

7. The programmable pump of claim 6, wherein the second chamber is filled with a propellant that acts upon the flexible membrane to push the fluid from the first chamber through first opening.

8. The programmable pump of claim 1, wherein during operation of the pump, fluid dispelled from the first chamber passes through the first opening, through into the valve block, into contact with the valve, out of the valve block, into the second opening and through the catheter.

9. The programmable pump of claim 8, wherein the control module further includes a first pressure sensor for monitoring the pressure of the fluid in the first chamber and a second pressure sensor for monitoring the pressure of the fluid in the valve block.

10. The programmable pump of claim 9, wherein the constant flow module further includes a fixed flow resistor.

11. The programmable pump of claim 10, wherein the fixed flow resistor includes a filter and a capillary, and fluid dispelled from the first chamber passes through the fixed flow resistor prior to passing through the first opening.

12. The programmable pump of claim 1, further comprising an enclosure top attached to the constant flow module and covering the control module.

13. The programmable pump of claim 1, wherein the control module further includes a processor for determining operation of the motor.

14. The programmable pump of claim 13, further comprising a circumferentially wrapped antenna extending around a perimeter of the constant flow module and being in communication with the processor.

15. The programmable pump of claim 1, wherein the control module further includes a positioning sensor capable of determining the positioning of the valve.

16. The programmable pump of claim 1, wherein the catheter includes a portion fixed to the constant flow module.

17. The programmable pump of claim 1, further comprising a union nut screwed to the constant flow module and holding the control module to the constant flow module.

18. The programmable pump of claim 17, further comprising a gasket held between the constant flow module and control module.

19. The programmable pump of claim 1, wherein the control module further includes first and second pressure sensors, first and second batteries, a circuit board, and a buzzer.

20. The programmable pump of claim 19, wherein the first and second pressure sensors, first and second batteries, circuit board, buzzer and stepper motor are electrically connected to each other via a flexible conductive element.

* * * * *